US009266983B2

United States Patent
Li et al.

(10) Patent No.: US 9,266,983 B2
(45) Date of Patent: Feb. 23, 2016

(54) CATALYST COMPOSITION AND PROCESS FOR ETHYLENE OLIGOMERIZATION

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Tonglin Li, Beijing (CN); Mingfang Zheng, Beijing (CN); Jun Liu, Beijing (CN); Huaijie Wang, Beijing (CN); Haiying Zhang, Beijing (CN); Weizhen Li, Beijing (CN); Jilong Wang, Beijing (CN); Yuling Piao, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 0 days.

(21) Appl. No.: 14/254,277

(22) Filed: Apr. 16, 2014

(65) Prior Publication Data

US 2014/0316087 A1 Oct. 23, 2014

(30) Foreign Application Priority Data

| Apr. 17, 2013 | (CN) | 2013 1 0132839 |
| Apr. 17, 2013 | (CN) | 2013 1 0132911 |
| Apr. 17, 2013 | (CN) | 2013 1 0133037 |
| Aug. 9, 2013 | (CN) | 2013 1 0347221 |
| Aug. 9, 2013 | (CN) | 2013 1 0347347 |
| Aug. 26, 2013 | (CN) | 2013 1 0376576 |
| Sep. 16, 2013 | (CN) | 2013 1 0421815 |
| Oct. 18, 2013 | (CN) | 2013 1 0492966 |

(51) Int. Cl.
C08F 4/70 (2006.01)
C08F 110/02 (2006.01)
C07C 2/32 (2006.01)
C07F 15/02 (2006.01)

(52) U.S. Cl.
CPC ............... *C08F 110/02* (2013.01); *C07C 2/32* (2013.01); *C07F 15/025* (2013.01); *C07C 2531/14* (2013.01); *C07C 2531/18* (2013.01); *C07C 2531/30* (2013.01)

(58) Field of Classification Search
CPC .... C08F 4/60089; C08F 4/7042; C07F 15/02; C07F 15/025
USPC .................. 526/93, 91, 169.1, 161, 172, 352
See application file for complete search history.

(56) References Cited

U.S. PATENT DOCUMENTS

| 5,744,679 A * | 4/1998 | Marinangeli ............. C07C 2/36 585/502 |
| 6,395,668 B1 * | 5/2002 | van Baar et al. ............. 502/123 |
| 2010/0234548 A1 * | 9/2010 | Kolling ................. C07F 15/025 526/192 |
| 2013/0018214 A1 * | 1/2013 | Zheng .................... B01J 31/143 585/513 |
| 2013/0267708 A1 * | 10/2013 | Liu ........................ B01J 31/183 546/10 |

FOREIGN PATENT DOCUMENTS

| CN | 102050841 A | * | 5/2011 | ............. C07F 15/06 |
| CN | 102485733 A | | 6/2012 | |
| CN | 102558241 A | | 7/2012 | |
| CN | 102558242 A | | 7/2012 | |
| CN | 102558243 A | | 7/2012 | |
| WO | WO 99/02472 | | 1/1999 | |

OTHER PUBLICATIONS

Small, B.L.; Brookhart, M. J. Am. Chem. Soc. 1998, 120, 7143-7144.*
Sun et al. Organometallics 2006, 25, 666-677.*
Jie et al. J. Molecular Catal. A: Chemical 2007, 269, 85-96.*
Zhang et al. J. Molecular Catal. A: Chemical 2010, 320, 92-96.*
Jie et al. Eur. J. Inorg. Chem. 2007, 35, 5584-5598.*
George J.P. Britovsek et al., "Novel Olefin Polymerization Catalysts Based on Iron and Cobalt," Chem. Commun., 1998, pp. 849-850.

(Continued)

*Primary Examiner* — Rip A Lee

(74) *Attorney, Agent, or Firm* — Buchanan Ingersoll & Rooney PC

(57) ABSTRACT

The present disclosure provides a catalyst composition for ethylene oligomerization including an imino ferrous complex shown in Formula (I) as the main catalyst, an aluminum-containing cocatalyst, water, and an organic solvent:

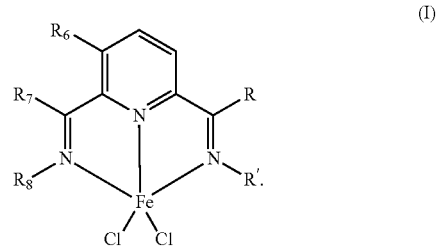

According to the present disclosure, a higher oligomerization activity can be obtained with the catalyst composition than with a catalyst composition system in the prior art which contains no water. Moreover, when the catalyst composition according to the present disclosure is used, a high selectivity of α-olefins is obtainable. Besides, the catalyst composition according to the present disclosure can enable rapid initiation, stable operation, and good repeatability of the oligomerization reaction. According to the present disclosure, a high oligomerization activity can be obtained even at a rather low ratio of Al/Fe, or at a low reaction temperature.

24 Claims, No Drawings

(56) References Cited

OTHER PUBLICATIONS

George J.P. Britovsek et al., "Oligomerisation of Ethylene by Bis(imino)Pyridyliron and -Cobalt Complexes," Chem. Eur. J., 2000, vol. 6, No. 12, pp. 2221-2231.

Brooke L. Small et al., "Iron-Based Catalysts with Exceptionally High Activities and Selectivites for Oligomerization of Ethylene to Linear αOlefins," J. Am. Chem. Soc., 1998, vol. 120, pp. 7143-7144.

Williams et al., "Drying of Organic Solvents: Quantitative Evaluation of the Efficiency of Several Desiccants", JOC Article, 2010, 75 (24), pp. 8351-8354. American Chemical Society.

Search Report and Written Opinion issued on Feb. 4, 2015, by the Dutch Patent Office in Dutch Application No. 2012643, with a partial English translation thereof. (10 pages).

* cited by examiner

CATALYST COMPOSITION AND PROCESS FOR ETHYLENE OLIGOMERIZATION

FIELD OF THE INVENTION

The present disclosure relates to a field of olefin polymerization, in particular to a catalyst composition used in a process of ethylene oligomerization. The present disclosure further relates to use of the catalyst composition.

BACKGROUND OF THE INVENTION

Linear alpha olefins (LAOS) are widely used in a wide range of applications, such as ethylene comonomers, intermediates in production of surfactants, plasticizer alcohols, synthetic lubricants and oil additives, etc. Recently, with the development of the polyolefin industry, the worldwide demand for alpha olefins grows rapidly. Currently, most alpha olefins are prepared based on ethylene oligomerization. Common catalysts used in ethylene oligomerization mainly include nickel-, chromium-, zirconium-, and alumina-based catalyst systems, and so on. Recently, iron (II) and cobalt (II) based catalysts bearing imino-pyridyl tridentate ligands for catalyzing ethylene oligomerization have been reported respectively by Brookhart's group (see Brookhart M. et al, J. Am. Chem. Soc., 1998, 120, 7143-7144, and WO99/02472) and Gibson's group (see Gibson V. C. et al, Chem. Commun., 1998, 849-850, and Chem. Eur. J., 2000, 2221-2231), in which both the catalytic activity and selectivity of alpha olefins are high.

Prior arts teach that water is rather harmful to ethylene oligomerization. The oligomerization process at present, therefore, demands an extremely anhydrous and oxygen-free environment, in which, however, initiation, stability, and repeatability of oligomerization reactions are difficult or poor.

The present disclosure expects to provide a technical solution that can overcome prejudices against water in the prior art relating to the oligomerization process. When a catalyst composition containing water is provided for ethylene oligomerization, a high oligomerization activity can actually be obtained even at a rather low ratio of aluminum to iron and/or a low temperature.

SUMMARY OF THE INVENTION

To overcome the defects in the prior art, the inventor of the present disclosure has conducted extensive and in-depth researches, and surprisingly found that a high oligomerization activity can be obtained using a catalyst composition containing an imino ferrous complex shown in Formula (I) as the main catalyst, an aluminum-containing cocatalyst, water, and an organic solvent. The catalyst composition can even enable a high oligomerization activity at a rather low ratio of Al/Fe. Furthermore, the oligomerization reaction is of rapid initiation, stable operation, and good repeatability. As a result, technical prejudices held by persons skilled in the art against water relating to oligomerization are overcome, and unexpected technical effects are obtained.

According to one aspect of the present disclosure, it provides a catalyst composition for ethylene oligomerization, comprising an imino ferrous complex as shown in Formula (I) as the main catalyst, an aluminum-containing cocatalyst, water, and an organic solvent:

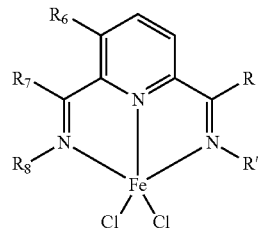

(I)

In Formula (I), R is selected from hydrogen, oxygen, and $(C_1-C_{10})$ linear alkyl, $(C_3-C_{10})$ branched alkyl, $(C_6-C_{20})$ aryl, $(C_7-C_{20})$ aralkyl, and $(C_7-C_{20})$ alkaryl groups. And R' is selected from substituted or unsubstituted $(C_6-C_{20})$ aryl, $(C_7-C_{20})$ aralkyl, $(C_7-C_{20})$ alkaryl groups. R and R' is optionally bonded to or not to form a ring.

$R_6$ is selected from hydrogen and saturated or unsaturated $(C_1-C_5)$ hydrocarbyl groups. $R_7$ is selected from saturated or unsaturated $(C_1-C_5)$ hydrocarbyl groups. $R_6$ and $R_7$ is optionally bonded to or not to form a ring. $R_8$ is selected from saturated or unsaturated $(C_1-C_5)$ hydrocarbyl, $(C_6-C_{20})$ aryl, $(C_7-C_{20})$ aralkyl, and $(C_7-C_{20})$ alkaryl groups. $R_7$ and $R_8$ are optionally bonded to or not to form a ring.

In one specific embodiment of the above catalyst composition, in Formula (I), R is selected from hydrogen, oxygen, and $(C_1-C_5)$ linear alkyl, $(C_3-C_6)$ branched alkyl, $(C_6-C_{10})$ aryl, $(C_7-C_{10})$ aralkyl, and $(C_7-C_{10})$ alkaryl groups; and R' is selected from substituted or unsubstituted phenyl, naphthyl, $(C_7-C_{20})$ aralkyl, and $(C_7-C_{20})$ alkaryl groups.

$R_6$ is selected from hydrogen, and saturated or unsaturated $(C_1-C_3)$ hydrocarbyl groups. $R_7$ is selected from saturated or unsaturated $(C_1-C_3)$ hydrocarbyl groups, $R_6$ and $R_7$ optionally being bonded to or not to form a ring. And $R_8$ is selected from saturated or unsaturated $(C_1-C_3)$ hydrocarbyl, $(C_6-C_{10})$ aryl, $(C_7-C_{10})$ aralkyl, and $(C_7-C_{10})$ alkaryl groups. $R_7$ and $R_8$ are optionally bonded to or not to form a ring.

In one specific embodiment of the above catalyst composition, based on weight of the organic solvent, the catalyst composition has a content of water in the range from 5 to 450 ppm, preferably from 5 to 350 ppm, more preferably 20 to 260 ppm, and further preferably from 50 to 200 ppm.

According to one specific embodiment of the catalyst composition of the present disclosure, the main catalyst imino ferrous complex has a general formula as shown in Formula (II):

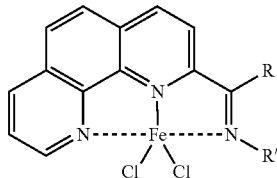

(II)

In Formula (II), R is selected from hydrogen, oxygen, and $(C_1-C_{10})$ linear alkyl, $(C_3-C_{10})$ branched alkyl, $(C_6-C_{20})$ aryl, $(C_7-C_{20})$ aralkyl, and $(C_7-C_{20})$ alkaryl groups, preferably from hydrogen, and $(C_1-C_5)$ linear alkyl, $(C_3-C_6)$ branched alkyl, $(C_6-C_{10})$ aryl, $(C_7-C_{10})$ aralkyl, and $(C_7-C_{10})$ alkaryl groups; and R' is selected from substituted or unsubstituted $(C_6-C_{20})$ aryl, $(C_7-C_{20})$ aralkyl, $(C_7-C_{20})$ alkaryl groups, preferably from substituted or unsubstituted phenyl, naphthyl, $(C_7-C_{20})$ aralkyl, and $(C_7-C_{20})$ alkaryl groups.

In one preferred embodiment of the above catalyst composition, the main catalyst imino ferrous complex has a general formula as shown in Formula (III):

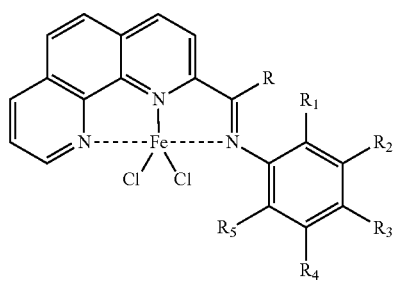

(III)

In Formula (III), $R_1$ to $R_5$ each are independently selected from hydrogen, ($C_1$-$C_6$) alkyl groups, halogens, ($C_1$-$C_6$) alkoxy or nitro groups; and R is selected from hydrogen, ($C_1$-$C_5$) linear alkyl, ($C_3$-$C_6$) branched alkyl, ($C_6$-$C_{10}$) aryl, ($C_7$-$C_{10}$) aralkyl, and ($C_7$-$C_{10}$) alkaryl groups. In one specific embodiment, in Formula (III), R is selected from hydrogen, and methyl, ethyl, propyl, isopropyl, butyl, isobutyl, tert-butyl, pentyl, phenyl, benzyl, tolyl, and phenethyl groups. And $R_1$ to $R_5$ each are independently selected from hydrogen, methyl, ethyl, n-propyl, and isopropyl groups, fluorine, chlorine, bromine, and methoxyl, ethoxyl and nitro groups. Preferably, $R_1$ and $R_5$ are both ethyl groups, and $R_2$ to $R_4$ all hydrogen.

According to another specific embodiment of the catalyst composition of the present disclosure, the main catalyst imino ferrous complex has a general formula as shown in Formula (IV):

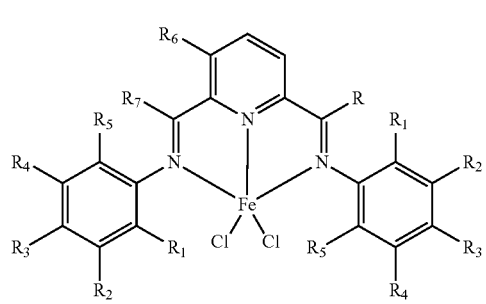

(IV)

In Formula (IV), $R_7$ is selected from ($C_1$-$C_5$) alkyl groups. R is selected from hydrogen, oxygen, and ($C_1$-$C_5$) alkyl groups. $R_1$ to $R_5$ each are independently selected from hydrogen, ($C_1$-$C_6$) alkyl groups, halogens, and ($C_1$-$C_6$) alkoxy or nitro groups. R is optionally bounded to $R_1$ or to a carbon atom connected to $R_1$ to or not to form a ring. In one specific embodiment, in Formula (IV), $R_1$ to $R_5$ each are independently selected from hydrogen, methyl, ethyl, n-propyl, and isopropyl groups, fluorine, chlorine, bromine, and methoxyl, ethoxyl and nitro groups. Preferably, $R_1$ and $R_5$ are both selected from hydrogen, and methyl and ethyl groups, and $R_2$ to $R_4$ are each hydrogen. When $R_1$ is hydrogen, R is bounded to a carbon atom connected to $R_1$ to or not to form a ring.

According to one specific embodiment of the catalyst composition of the present disclosure, the molar ratio of aluminum in the cocatalyst to iron in the main catalyst ranges from 30:1 to less than 900:1, preferably from 100:1 to 700:1, and more preferably from 148:1 to 196:1.

According to another specific embodiment of the catalyst composition of the present disclosure, the aluminum-containing cocatalyst is selected from aluminoxanes and alkylaluminum compounds, preferably from alkylaluminum compounds. The alkylaluminum compounds have a general formula of $AlR_nX_m$, wherein R is a linear or branched ($C_1$-$C_8$) alkyl group; and X is a halogen, preferably chlorine or bromine, with n being an integral ranging from 1 to 3, m an integral ranging from 0 to 2, and m+n=3. The alkylaluminum compounds are preferably selected from trimethylaluminum, triethylaluminum, tripropylaluminum, triisobutylaluminum, tri-n-hexyl aluminum, tri-n-octyl aluminum, diethyl aluminum chloride, and ethyl aluminum dichloride, more preferably triethylaluminum. The aluminoxanes are ($C_1$-$C_4$) alkylaluminoxanes with linear or branched ($C_1$-$C_4$) alkyl groups, preferably selected from methylaluminoxane, modified methylaluminoxane, ethylaluminoxane, and isobutyl aluminoxane, and more preferably methylaluminoxane.

According to still another specific embodiment of the catalyst composition of the present disclosure, based on volume of the organic solvent, the catalyst composition has a content of the main catalyst in the range from 2 to 500 μmol, preferably from 20 to 100 μmol/L.

According to further another specific embodiment of the catalyst composition of the present disclosure, the organic solvent is selected from toluene, cyclohexane, diethyl ether, tetrahydrofuran, ethanol, benzene, xylene, and dichloromethane, preferably from toluene and xylene.

According to another aspect of the present disclosure, it provides a process for ethylene oligomerization, comprising performing the ethylene oligomerization in the presence of the catalyst composition according to the first aspect of the present disclosure, wherein the catalyst composition comprises an imino ferrous complex as shown in Formula (I) as the main catalyst, an aluminum-containing cocatalyst, water, and an organic solvent.

According to one specific embodiment of the oligomerization process, the process is performed at a temperature in the range from −20° C. to 150° C., preferably from 0° C. to 80° C., and more preferably from 5° C. to 35° C. In one preferred embodiment, the reaction can be performed at a temperature in the range from 5° C. to 50° C.

In still another preferred embodiment of the ethylene oligomerization, the process comprises mixing the main catalyst and the cocatalyst under ethylene atmosphere.

A higher oligomerization activity can be obtained with the catalyst composition according to the present disclosure which comprises the imino ferrous complex shown in Formula (I) as the main catalyst, the aluminum-containing cocatalyst, water, and the organic solvent, than with a catalyst composition system in the prior art which contains no water. Moreover, when the catalyst composition according to the present disclosure is used, a high selectivity of α-olefins is obtainable. Besides, the catalyst composition according to the present disclosure can enable rapid initiation, stable operation, and good repeatability of the oligomerization reaction. According to the present disclosure, a high oligomerization activity can be obtained even at a rather low ratio of Al/Fe, or at a low reaction temperature. The present disclosure overcomes technical prejudices held by persons skilled in the art and achieves unexpected technical effects.

DETAILED DESCRIPTION OF THE EMBODIMENTS

According to one aspect of the present disclosure, it provides a catalyst composition for ethylene oligomerization comprising an imino ferrous complex shown in Formula (I) as the main catalyst, an aluminum-containing cocatalyst, water, and an organic solvent.

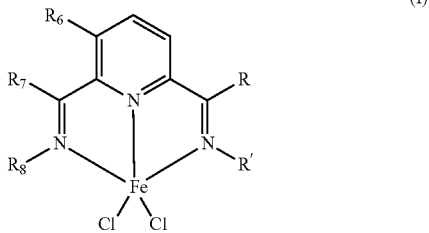

In Formula (I), R is selected from hydrogen, oxygen, and $(C_1-C_{10})$ linear alkyl, $(C_3-C_{10})$ branched alkyl, $(C_6-C_{20})$ aryl, $(C_7-C_{20})$ aralkyl, and $(C_7-C_{20})$ alkaryl groups; and R' is selected from substituted or unsubstituted $(C_6-C_{20})$ aryl, $(C_7-C_{20})$ aralkyl, $(C_7-C_{20})$ alkaryl groups, R and R' optionally being bonded to or not to form a ring.

In Formula (I), $R_6$ is selected from hydrogen and saturated or unsaturated $(C_1-C_5)$ hydrocarbyl groups; $R_7$ is selected from saturated or unsaturated $(C_1-C_5)$ hydrocarbyl groups, $R_6$ and $R_7$ optionally being bonded to or not to form a ring; and $R_8$ is selected from saturated or unsaturated $(C_1-C_5)$ hydrocarbyl, $(C_6-C_{20})$ aryl, $(C_7-C_{20})$ aralkyl, and $(C_7-C_{20})$ alkaryl groups, $R_7$ and $R_8$ optionally being bonded to or not to form a ring.

In one specific embodiment of the above catalyst composition, in Formula (I), R is selected from hydrogen, oxygen, and $(C_1-C_5)$ linear alkyl, $(C_3-C_6)$ branched alkyl, $(C_6-C_{10})$ aryl, $(C_7-C_{10})$ aralkyl, and $(C_7-C_{10})$ alkaryl groups; and R' is selected from substituted or unsubstituted phenyl, naphthyl, $(C_7-C_{20})$ aralkyl, and $(C_7-C_{20})$ alkaryl groups. And $R_6$ is selected from hydrogen, and saturated or unsaturated $(C_1-C_3)$ hydrocarbyl groups; $R_7$ is selected from saturated or unsaturated $(C_1-C_3)$ hydrocarbyl groups, $R_6$ and $R_7$ optionally being bonded to or not to form a ring; and $R_8$ is selected from saturated or unsaturated $(C_1-C_3)$ hydrocarbyl, $(C_6-C_{10})$ aryl, $(C_7-C_{10})$ aralkyl, and $(C_7-C_{10})$ alkaryl groups, $R_7$ and $R_8$ optionally being bonded to or not to form a ring.

The catalyst composition according to the present disclosure contains water, but, when used in an ethylene oligomerization process, can lead to a high reaction activity, and rapid initiation, stable operation, and good repeatability of the reaction, with a high selectivity of α-olefins. In the present disclosure, especially in medium-level tests of ethylene oligomerization and relevant industrial production, anhydrous environment is not only unnecessary, but a certain amount of water is actually required to be added into the organic solvent to accomplish corresponding reactions.

The catalyst composition according to the present disclosure promotes a high ethylene oligomerization activity and high selectivity of α-olefins.

In the present disclosure, the term "saturated or unsaturated $(C_1-C_5)$ hydrocarbyl groups" refers to saturated or unsaturated hydrocarbyl groups with 1 to 5 carbon atoms, such as methyl, ethyl, vinyl, propyl, isopropyl, allyl, propenyl, butyl, isobutyl, tert-butyl, and butenyl groups, etc.

In the catalyst composition according to the present disclosure, based on weight of the organic solvent, the catalyst composition has a content of water in the range from 5 to 450 ppm (i.e., based on 1 g of the organic solvent, $5×10^{-6}$ to $450×10^{-6}$ g of water is contained in the catalyst composition), preferably from 5 to 350 ppm, more preferably 20 to 260 ppm, and further preferably from 50 to 200 ppm. The catalyst composition, having water within the above content ranges, promotes even higher activity of ethylene oligomerization.

In the catalyst composition according to the present disclosure, the amount of the main catalyst and that of the cocatalyst can be selected according to actual process conditions such as the production scale, equipment, etc. In one specific embodiment of the catalyst composition, based on volume of the organic solvent, the catalyst composition has a content of the main catalyst in the range from 2 μmol/L to 500 μmol/L (i.e., based on 1 L of the organic solvent, the catalyst composition contains $2×10^{-6}$ mol to $500×10^{-6}$ mol of the main catalyst), preferably from 20 μmol/L to 100 μmol/L.

According to one specific embodiment of the catalyst composition of the present disclosure, the main catalyst imino ferrous complex has a general formula as shown in Formula (II).

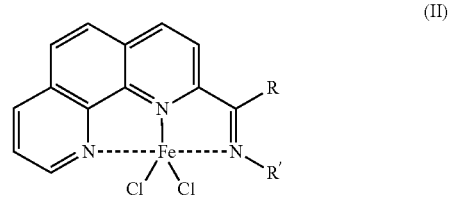

In Formula (II), R is selected from hydrogen, oxygen, and $(C_1-C_{10})$ linear alkyl, $(C_3-C_{10})$ branched alkyl, $(C_6-C_{20})$ aryl, $(C_7-C_{20})$ aralkyl, and $(C_7-C_{20})$ alkaryl groups, preferably from hydrogen, and $(C_1-C_5)$ linear alkyl, $(C_3-C_6)$ branched alkyl, $(C_6-C_{10})$ aryl, $(C_7-C_{10})$ aralkyl, and $(C_7-C_{10})$ alkaryl groups; and R' is selected from substituted or unsubstituted $(C_6-C_{20})$ aryl, $(C_7-C_{20})$ aralkyl, $(C_7-C_{20})$ alkaryl groups, preferably from substituted or unsubstituted phenyl, naphthyl, $(C_7-C_{20})$ aralkyl, and $(C_7-C_{20})$ alkaryl groups. Said $(C_7-C_{20})$ aralkyl groups comprise diphenyl methyl group. The structure as shown in Formula (II) is formed when both $R_6$ and $R_7$, and $R_7$ and $R_8$ in Formula (I) are bonded to form benzene rings.

According to one specific embodiment of the catalyst composition of the present disclosure, the main catalyst imino ferrous complex has a general formula as shown in Formula (III).

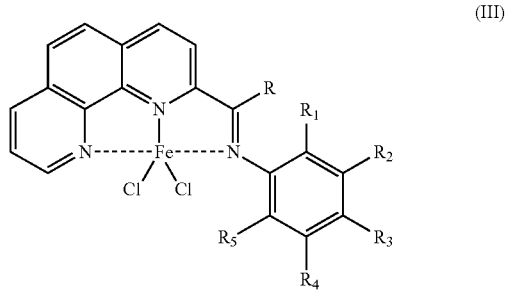

In Formula (III), $R_1$ to $R_5$ each are independently selected from hydrogen, $(C_1-C_6)$ alkyl groups, halogens, $(C_1-C_6)$ alkoxy or nitro groups; and R is selected from hydrogen, $(C_1-C_5)$ linear alkyl, $(C_3-C_6)$ branched alkyl, $(C_6-C_{10})$ aryl, $(C_7-C_{10})$ aralkyl, and $(C_7-C_{10})$ alkaryl groups. That is, when R' in Formula (II) is an alkyl phenyl group, the structure as shown in Formula (III) can be obtained. In one specific embodiment, in Formula (III), R can be selected from hydrogen, and methyl, ethyl, propyl, isopropyl, butyl, isobutyl, tert-butyl, pentyl, phenyl, benzyl, tolyl, and phenethyl groups; and $R_1$ to $R_5$ each are independently selected from hydrogen, methyl, ethyl, n-propyl, and isopropyl groups, fluorine, chlorine, bromine, and methoxyl, ethoxyl and nitro groups, preferably, $R_1$ and $R_5$ both being ethyl groups, and $R_2$ to $R_4$ all hydrogen.

In the present disclosure, the term "$(C_1-C_6)$ alkyl groups" refers to saturated linear or branched alkyl groups with 1-6 carbon atoms. Said $(C_1-C_6)$ alkyl groups include methyl, ethyl, n-propyl, isopropyl, n-butyl, isobutyl, sec-butyl, tert-butyl, n-pentyl, sec-pentyl, n-hexyl, and sec-hexyl groups, preferably methyl, ethyl, n-propyl, and isopropyl groups.

In the present disclosure, the term "$(C_1-C_6)$ alkoxyl groups" refers to the groups obtained from the bond of a $(C_1-C_6)$ alkyl group with an oxygen atom. Said $(C_1-C_6)$ alkoxyl groups include methoxyl, ethoxyl, n-propoxyl, isopropoxyl, n-butoxyl, isobutoxyl, sec-butoxyl, tert-butoxyl, n-pentoxyl, sec-pentoxyl, n-hexyloxyl, and sec-hexyloxyl groups, preferably methoxyl and ethoxyl groups.

In the present disclosure, the term "halogens" includes F, Cl, Br, and I, preferably F, Cl, and Br.

According to one specific embodiment of the catalyst composition of the present disclosure, the main catalyst imino ferrous complex as shown in Formula (III) has one of the following structures.

(i)

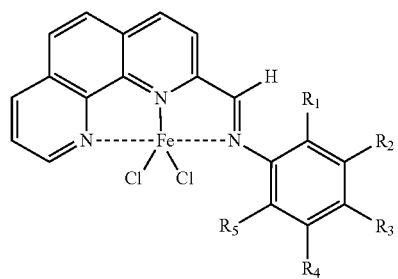

(ii)

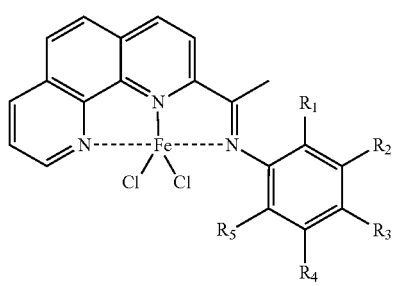

(iii)

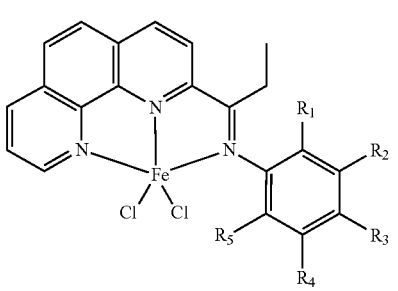

(iv)

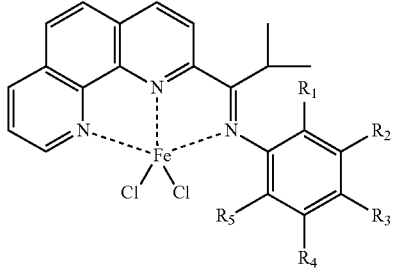

(v)

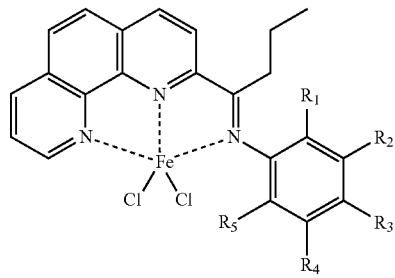

(vi)

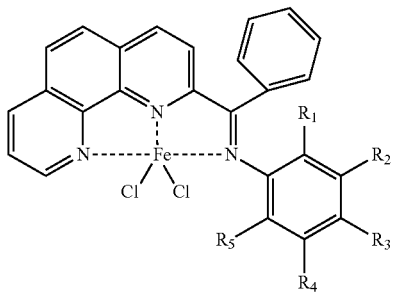

According to another specific embodiment of the catalyst composition of the present disclosure, the main catalyst imino ferrous complex has a general formula as shown in Formula (IV).

(IV)

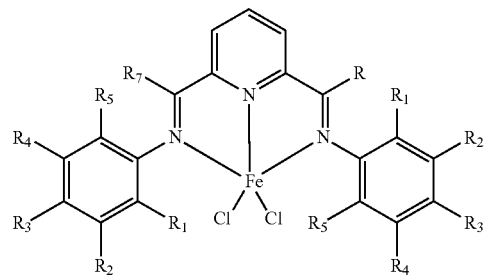

In Formula (IV), $R_7$ is selected from $(C_1-C_5)$ alkyl groups; R is selected from hydrogen, oxygen, and $(C_1-C_5)$ alkyl groups; and $R_1$ to $R_5$ each are independently selected from hydrogen, $(C_1-C_6)$ alkyl groups, halogens, and $(C_1-C_6)$ alkoxy or nitro groups, R being optionally bounded to $R_1$ or to a carbon atom connected to $R_1$ to or not to form a ring. When $R_8$ and R' in Formula (I) are alkyl phenyl groups, and $R_6$ in Formula (I) is hydrogen, the structure as shown in Formula (IV) can be obtained. In one specific embodiment, in Formula (IV), $R_1$ to $R_5$ each are independently selected from hydrogen, methyl, ethyl, n-propyl, and isopropyl groups, fluorine, chlorine, bromine, and methoxyl, ethoxyl and nitro groups.

Preferably, $R_1$ and $R_5$ are both selected from hydrogen, and methyl and ethyl groups, and $R_2$ to $R_4$ are each hydrogen. When $R_1$ is hydrogen, R is bounded to a carbon atom connected to $R_1$ to or not to form a ring.

According to one specific embodiment of the above catalyst composition, the main catalyst imino ferrous complex as shown in Formula (IV) has one of the following structures.

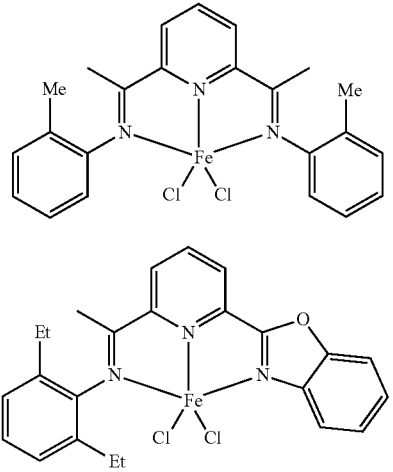

According to one specific embodiment of the catalyst composition of the present disclosure, the molar ratio of aluminum in the cocatalyst to iron in the main catalyst ranges from 30:1 to less than 900:1, preferably from 100:1 to 700:1, and more preferably from 148:1 to 196:1.

According to another specific embodiment of the catalyst composition of the present disclosure, the aluminum-containing cocatalyst is selected from aluminoxanes and alkylaluminum compounds, preferably from alkylaluminum compounds. The alkylaluminum compounds have a general formula of $AlR_nX_m$, herein R is a linear or branched ($C_1$-$C_8$) alkyl group; and X is a halogen, preferably chlorine or bromine, with n being an integral ranging from 1 to 3, m an integral ranging from 0 to 2, and m+n=3. The alkylaluminum compounds are preferably selected from trimethylaluminum, triethylaluminum, tripropylaluminum, triisobutylaluminum, tri-n-hexyl aluminum, tri-n-octyl aluminum, diethyl aluminum chloride, and ethyl aluminum dichloride, more preferably triethylaluminum. The aluminoxanes are ($C_1$-$C_4$) alkylaluminoxanes with linear or branched ($C_1$-$C_4$) alkyl groups, preferably selected from methylaluminoxane, modified methylaluminoxane, ethylaluminoxane, and isobutyl aluminoxane, and more preferably methylaluminoxane.

According to still another specific embodiment of the catalyst composition of the present disclosure, based on volume of the organic solvent, the catalyst composition has a content of the main catalyst in the range from 2 μmol/L to 500 μmol/L, preferably from 20 μmol/L, to 100 μmol/L.

According to still another specific embodiment of the catalyst composition of the present disclosure, the organic solvent is selected from toluene, cyclohexane, diethyl ether, tetrahydrofuran, ethanol, benzene, xylene, and dichloromethane, preferably from toluene and xylene.

Preparation of the main catalyst of the present disclosure is known in the prior art. For example, reference can be made to CN 102558243A for synthesis of the compounds as shown in Formula (II) or (III). CN 102558243A is incorporated into the present disclosure as a reference.

According to one specific embodiment of the present disclosure, the main catalyst 2-acetyl-1,10-phenanthroline aminal ferrous chloride complex as shown in Formula (ii) can be prepared by the process as disclosed in CN 102485733A with specific steps as follows.

Step a: synthesis of 2-acetyl-1,10-phenanthroline: 1,10-phenanthroline is reacted with $Et_3Al$. The resultant thereof successively goes through a hydrolysis reaction and then an oxidation reaction with nitrobenzene to obtain a compound as shown in Formula (b).

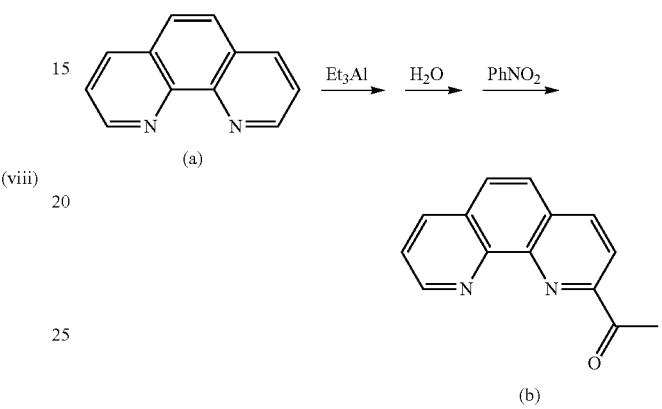

In order to prepare 2-acetyl-1,10-phenanthroline as shown in Formula (b), 1,10-phenanthroline is first reacted with $Et_3Al$ in the presence of an organic solvent, which can be selected from toluene, cyclohexane, diethyl ether, tetrahydrofuran, ethanol, benzene, xylene, dichloromethane, mixtures thereof, etc., preferably toluene. A 1,10-phenanthroline solution with a concentration of 10 g/L to 200 g/L is prepared with the above organic solvents. The reaction between 1,10-phenanthroline and $Et_3Al$ is commonly performed at a temperature in the range from −60° C. to −80° C., preferably from −60° C. to −70° C., favorably under protection of an inert gas, which is preferably selected as argon or nitrogen. Anhydrous or hydrous 1,10-phenanthroline, preferably anhydrous 1,10-phenanthroline, and $Et_3Al$ per se are selected as the raw materials for the above reaction with a molar ratio of 1,10-phenanthroline to $Et_3Al$ in the range from 1:0.5 to 1:4.5, preferably 1:2.0 to 1:2.6. Favorably, the reaction is carried out usually by adding, for example, dropwise adding $Et_3Al$ at a reaction temperature into the 1,10-phenanthroline solution. After the above addition is completed, the resulting mixture is stirred for 18 h to 28 h at the reaction temperature, preferably 18 to 20 h. Afterwards, the reaction temperature is heated up to 20° C. to 40° C., before the resulting mixture is stirred again for 5 h to 10 h, preferably 10 h to facilitate more complete reaction. Next, water (preferably deionized water) is added for hydrolysis at a temperature in the range from −60° C. to 0° C. For example, water, preferably deionized water, can be added into the resulting mixture at −30° C. for hydrolysis. There are bubbles during hydrolysis process, and the hydrolysis process is not to be stopped until no bubbles come out. In order to ensure more complete hydrolysis, the resulting mixture is heated again to 20° C. to 40° C. and stirred for 5 h to 10 h. Subsequently, the resultant is separated and an organic phase therein is taken out. In order to obtain the required product as much as possible, an organic solvent is preferably used for extraction of the inorganic phase in the resultant, and then the obtained organic phase is combined with the organic phase obtained through separation, wherein useful organic solvents can be ethyl acetate, acetone, dichloromethane, or a mixture thereof, preferably dichloromethane. The solvent is removed from the organic phase or combined organic phase under reduced pressure prior to addition of nitrobenzene therein for reflux (for example at 210° C.) for 10 h to 48 h, preferably 15 h to 24 h. After that, the resultant is filtered, and the solvent is removed under reduced pressure. A mixture solution of ethyl acetate and petroleum ether with a volume ratio therebetween in the range from 1:1 to 1:5, preferably 1:2 is used as an eluent to perform silica column chromatography to obtain a solid product, i.e., the compound as shown in Formula (b). In the above synthesis step, the molar ratio of 1,10-phenanthroline to nitrobenzene is in the range from 1:0.5 to 1:30, preferably from 1:15 to 1:20.

Step b: synthesis of 2-acetyl-1,10-phenanthroline aminal ligand: the compound as shown in Formula (b) is reacted with the compound as shown in Formula (c) in the presence of p-toluenesulfonic acid as the catalyst to obtain the compound as shown in Formula (d).

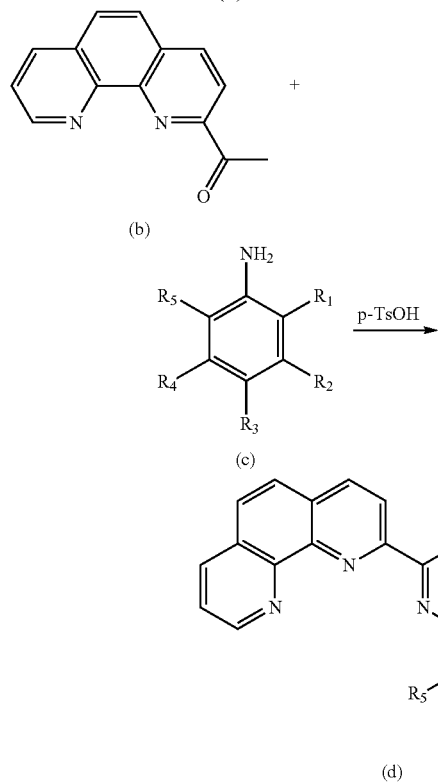

For definitions of $R_1$ to $R_5$, references can be made to definitions relating to Formula (III).

The product ligand as shown in Formula (d) is prepared by reacting 2-acetyl-1,10-phenanthroline obtained in Step a with substituted anline as shown in Formula (c) in a container in the presence of an organic solvent containing no water or oxygen, wherein the molar ratio of 2-acetyl-1,10-phenanthroline to substituted anline as shown in Formula (c) is in the range from 1:1 to 1:5. Said organic solvent can be selected from toluene, cyclohexane, diethyl ether, tetrahydrofuran, ethanol, benzene, xylene, dichloromethane, mixtures thereof, etc., preferably toluene. The reaction is carried out under reflux in the presence of p-toluenesulfonic acid (p-TsOH) as the catalyst at, for example 110° C., wherein the mass ratio of p-TsOH to the total amounts of the reactants (i.e., the compounds as shown in Formulae (b) and (c)) is in the range from 0.001:1 to 0.02:1; and the reaction time is in the range from 5 h to 10 h. The reaction is monitored by TLC. Upon completion of the reaction of 2-acetyl-1,10-phenanthroline, the solvent is removed under reduced pressure. After that, a mixture solution of ethyl acetate and petroleum ether with a volume ratio therebetween in the range from 1:1 to 1:9, preferably 1:4 is used as an eluent to perform silica column chromatography to obtain the target product, i.e., the compound as shown in Formula (d). The target product is characterized by nuclear magnetism and mass spectrum.

In one preferred embodiment of the present disclosure, the substituted anline as shown in Formula (c) can be an anline substituted by 1 to 5, preferably 1 to 4, and more preferably 1 to 3 identical or different substituent groups selected from $(C_1-C_6)$ alkyl and $(C_1-C_6)$ alkoxy groups, halogens, and nitro groups, for example, 2-methylaniline, 3-methylaniline, 4-methylaniline, 2,3-dimethylaniline, 2,4-dimethylaniline, 2,5-dimethylaniline, 2,6-dimethylaniline, 3,4-dimethylaniline, 3,5-dimethyl aniline, 2,4,6-trimethyl aniline, 4-bromo-2,6-dimethylaniline, 2-ethylaniline, 2-ethyl-6-methylaniline, 2-isopropylaniline, 2,6-diethylaniline, 2,6-diisopropyl aniline, 2-fluoroaniline, 2-fluoro-4-methylaniline, 2-fluoro-5-methylaniline, 2,4-difluoro-aniline, 2,5-difluoro-aniline, 2,6-difluoro-aniline, 3,4-difluoro-aniline, 2,3,4-trifluoroaniline, 2,4,5-trifluoroaniline, 2,4,6-trifluoroaniline, 2,3,4,5,6-pentafluoroaniline, 3-chloroaniline, 2,6-dichloroaniline, 2,3,4-trichloroaniline, 2,4,5-trichloroaniline, 2,4,6-trichloroaniline, 2-bromoaniline, 2-bromo-4-methylaniline, 2-bromo-4-fluoroaniline, 4-bromo-2-fluoroaniline, 2,6-dibromoaniline, 2,6-dibromo-4-methylaniline, 2,6-dibromo-4-chloroaniline, 2,4,6-tribromoaniline, 2-bromo-6-chloro-4-fluoroaniline, 2-bromo-4-chloro-6-fluoroaniline, 2-bromo-4,6-difluoroaniline, 3-nitroaniline, 4-methoxyaniline, 2-methyl-4-methoxyaniline, and 4-ethoxyaniline, preferably 2,6-diethylaniline.

Step c: synthesis of 2-acetyl-1,10-phenanthroline aminal ferrous chloride complex: the compound as shown in Formula (d) is reacted with ferrous chloride to obtain the compound as shown in Formula (ii).

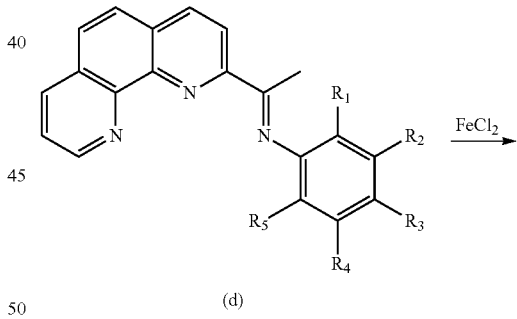

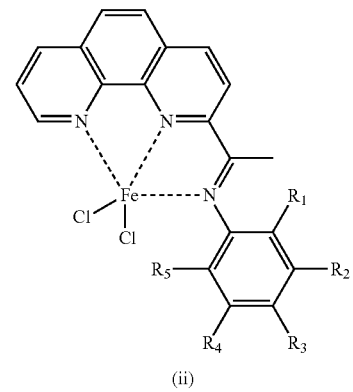

For definitions of $R_1$ to $R_5$, references can be made to definitions relating to Formula (III).

Under protection of an inert gas such as nitrogen, ferrous chloride is dissolved into an organic solvent containing no water or oxygen, so as to form a solution with a concentration of 0.001 g/ml to 0.1 g/ml, wherein the organic solvent can be selected from toluene, cyclohexane, diethyl ether, tetrahydrofuran, ethanol, benzene, xylene, dichloromethane, and mixtures thereof, preferably tetrahydrofuran. To obtain said ferrous chloride solution, hydrated ferrous chloride ($FeCl_2 \cdot 4H_2O$) can be used instead of ferrous chloride. 2-acetyl-1,10-phenanthroline aminal ligand (d) is separately dissolved into an organic solvent containing no water or oxygen to form a solution with a concentration of 0.01 g/ml to 0.1 g/ml, wherein the organic solvent can be selected from toluene, cyclohexane, diethyl ether, tetrahydrofuran, ethanol, benzene, xylene, dichloromethane, and mixtures thereof, preferably tetrahydrofuran. Subsequently, the above two solutions are combined (for example at room temperature) under protection of an inner gas such as nitrogen, and the resulting mixture is stirred for some time under protection of an inert gas such as nitrogen, for example, being stirred overnight at room temperature. The reaction is monitored by TLC. Upon completion of the reaction, conventional treatment methods of suction filtration, washing, drying, etc. are adopted to treat the reaction product to obtain the compound ligand as shown in Formula (ii). Said washing can be performed using an organic solvent such as anhydrous diethyl ether. The ligand is characterized by elemental analysis and infrared spectroscopy. In the synthesis step, the molar ratio of 2-acetyl-1,10-phenanthroline aminal ligand (d) to ferrous chloride is in the range from 1:1 to 1.2:1, preferably from 1.05:1 to 1.1:1.

According to one specific embodiment of the present disclosure, the main catalyst as shown in Formula (iv) can be prepared by the process as disclosed in CN 102558242A. Therefore, 2-isobutyryl-1,10-phenanthroline aminal ferrous chloride complex can be prepared by specific steps as follows.

Step a: synthesis of 2-isobutyryl-1,10-phenanthroline: 1,10-phenanthroline is reacted with $(i-C_4H_9)_3Al$. The resultant thereof successively goes through a hydrolysis reaction and then an oxidation reaction with nitrobenzene to obtain a compound as shown in Formula (b').

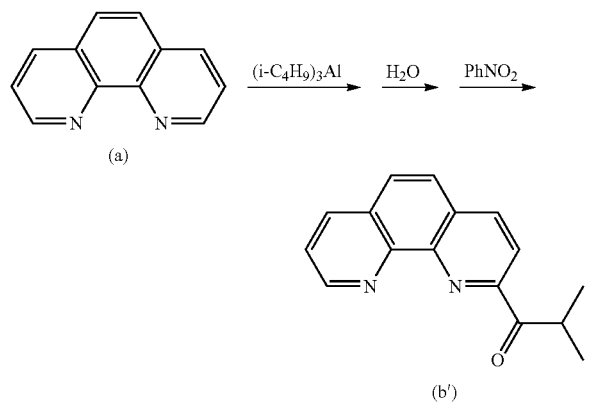

In order to prepare 2-isobutyryl-1,10-phenanthroline as shown in Formula (b'), 1,10-phenanthroline is first reacted with $(i-C_4H_9)_3Al$ in the presence of an organic solvent, which can be selected from toluene, cyclohexane, diethyl ether, tetrahydrofuran, ethanol, benzene, xylene, dichloromethane, mixtures thereof, etc., preferably toluene. A 1,10-phenanthroline solution with a concentration of 10 g/L to 200 g/L is prepared with the above organic solvents. The reaction between 1,10-phenanthroline and $(i-C_4H_9)_3Al$ is commonly performed at a temperature in the range from −60° C. to −80° C., preferably from −60° C. to −70° C., favorably under protection of an inert gas, which is preferably selected as argon or nitrogen. Anhydrous or hydrous 1,10-phenanthroline, preferably anhydrous 1,10-phenanthroline, and $(i-C_4H_9)_3Al$ per se are selected as the raw materials for the above reaction with a molar ratio of 1,10-phenanthroline to $(i-C_4H_9)_3Al$ in the range from 1:0.5 to 1:4.5, preferably 1:2.0 to 1:2.6. Favorably, the reaction is carried out usually by adding, for example, dropwise adding $(i-C_4H_9)_3Al$ at a reaction temperature into the 1,10-phenanthroline solution. After the above addition is completed, the resulting mixture is stirred for 18 h to 28 h at the reaction temperature, preferably 18 to 20 h. Afterwards, the reaction temperature is heated up to 20° C. to 40° C., before the resulting mixture is stirred again for 5 h to 10 h, preferably 10 h to facilitate more complete reaction. Next, water (preferably deionized water) is added for hydrolysis at a temperature in the range from −60° C. to 0° C. For example, water, preferably deionized water, can be added into the resulting mixture at −30° C. for hydrolysis. There are bubbles during hydrolysis process, and the hydrolysis process is not to be stopped until no bubbles come out. In order to ensure more complete hydrolysis, the resulting mixture is heated again to 20° C. to 40° C. and stirred for 5 h to 10 h. Subsequently, the resultant is separated and an organic phase therein is taken out. In order to obtain the required product as much as possible, an organic solvent is preferably used for extraction of the inorganic phase in the resultant, and then the organic phase is combined with the organic phase obtained through separation, wherein useful organic solvents can be ethyl acetate, acetone, dichloromethane, or a mixture thereof, preferably dichloromethane. The solvent is removed from the organic phase or combined organic phase under reduced pressure prior to addition of nitrobenzene therein for reflux (for example at 210° C.) for 10 h to 48 h, preferably 15 h to 24 h. After that, the resultant is filtered, and the solvent is removed under reduced pressure. A mixture solution of ethyl acetate and petroleum ether with a volume ratio therebetween in the range from 1:1 to 1:5, preferably 1:2 is used as an eluent to perform silica column chromatography to obtain a solid product, i.e., the compound as shown in Formula (b'). In the above synthesis step, the molar ratio of 1,10-phenanthroline to nitrobenzene is in the range from 1:0.5 to 1:30, preferably from 1:15 to 1:20.

Step b: synthesis of 2-isobutyryl-1,10-phenanthroline aminal ligand: the compound as shown in Formula (b') is reacted with the compound as shown in Formula (c) in the presence of p-toluenesulfonic acid as the catalyst to obtain the compound as shown in Formula (d').

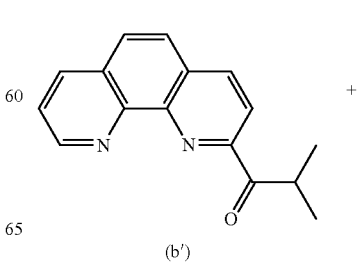

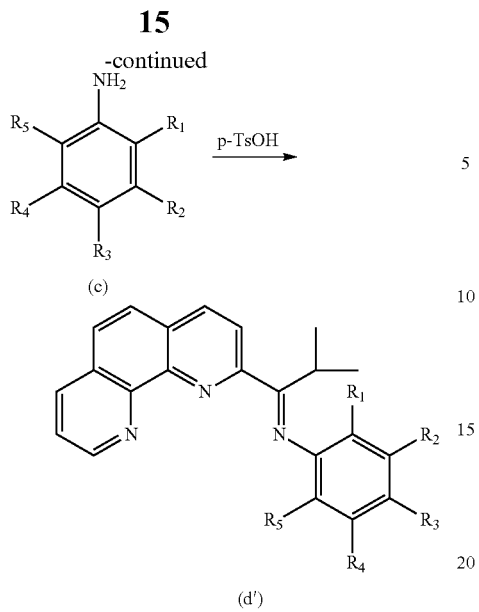

(d')

For definitions of $R_1$ to $R_5$, references can be made to definitions relating to Formula (III).

The product ligand as shown in Formula (d') is prepared by reacting 2-isobutyryl-1,10-phenanthroline obtained in Step a with substituted aniline as shown in Formula (c) in a container in the presence of an organic solvent containing no water or oxygen, wherein the molar ratio of 2-isobutyryl-1,10-phenanthroline to substituted aniline as shown in Formula (c) is in the range from 1:1 to 1:5. Said organic solvent can be selected from toluene, cyclohexane, diethyl ether, tetrahydrofuran, ethanol, benzene, xylene, dichloromethane, mixtures thereof, etc., preferably toluene. The reaction is carried out under reflux in the presence of p-toluenesulfonic acid (p-TsOH) as the catalyst at, for example 110° C., wherein the mass ratio of p-TsOH to the total amount of the reactants (i.e., the compounds as shown in Formulae (b') and (c)) is in the range from 0.001:1 to 0.02:1; and the reaction time is in the range from 5 h to 10 h. The reaction is monitored by TLC. Upon completion of the reaction of 2-isobutyryl-1,10-phenanthroline, the solvent is removed under reduced pressure. After that, a mixture solution of ethyl acetate and petroleum ether with a volume ratio therebetween in the range from 1:1 to 1:9, preferably 1:4 is used as an eluent to perform silica column chromatography to obtain the target product, i.e., the compound as shown in Formula (d'). The target product is characterized by nuclear magnetism and mass spectrum.

Step c: synthesis of 2-isobutyryl-1,10-phenanthroline aminal ferrous chloride complex: the compound as shown in Formula (d') is reacted with ferrous chloride to obtain the compound as shown in Formula (iv).

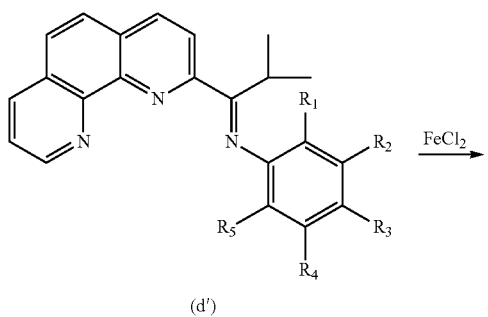

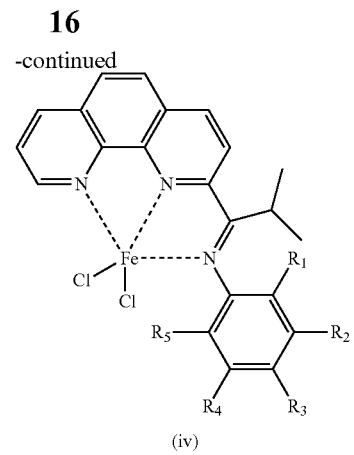

(iv)

For definitions of $R_1$ to $R_5$, references can be made to definitions relating to Formula (III).

Under protection of an inert gas such as nitrogen, ferrous chloride is dissolved into an organic solvent containing no water or oxygen, so as to form a solution with a concentration of 0.001 g/ml to 0.1 g/ml, wherein the organic solvent can be selected from toluene, cyclohexane, diethyl ether, tetrahydrofuran, ethanol, benzene, xylene, dichloromethane, and mixtures thereof, preferably tetrahydrofuran. To obtain said ferrous chloride solution, hydrated ferrous chloride ($FeCl_2 \cdot 4H_2O$) can also be used instead of ferrous chloride. 2-isobutyryl-1,10-phenanthroline aminal ligand (d') is separately dissolved into an organic solvent containing no water or oxygen to form a solution with a concentration of 0.01 g/ml to 0.1 g/ml, wherein the organic solvent can be selected from toluene, cyclohexane, diethyl ether, tetrahydrofuran, ethanol, benzene, xylene, dichloromethane, and mixtures thereof, preferably tetrahydrofuran. Subsequently, the above two solutions are combined (for example at room temperature) under protection of an inner gas such as nitrogen, and the resulting mixture is stirred for some time under protection of an inert gas such as nitrogen, for example, being stirred overnight at room temperature. The reaction is monitored by TLC. Upon completion of the reaction, conventional treatment methods of suction filtration, washing, drying, etc. are adopted to treat the reaction product to obtain the compound ligand as shown in Formula (iv). Said washing can be performed using an organic solvent such as anhydrous diethyl ether. The ligand is characterized by elemental analysis and infrared spectroscopy. In the synthesis step, the molar ratio of 2-isobutyryl-1,10-phenanthroline aminal ligand (d') to ferrous chloride is in the range from 1:1 to 1.2:1, preferably from 1.05:1 to 1.1:1.

According to one specific embodiment of the present disclosure, the main catalyst as shown in Formula (iii) can be prepared by the process as disclosed in CN 102558241A. Therefore, 2-n-propyl-acyl-1,10-phenanthroline aminal ferrous chloride complex can be prepared by the specific steps as follows.

Step a: synthesis of 2-n-propyl-acyl-1,10-phenanthroline: 1,10-phenanthroline is reacted with $(n-C_3H_7)_3Al$. The resultant thereof successively goes through a hydrolysis reaction and then oxidation reaction with nitrobenzene to obtain a compound as shown in Formula (b'').

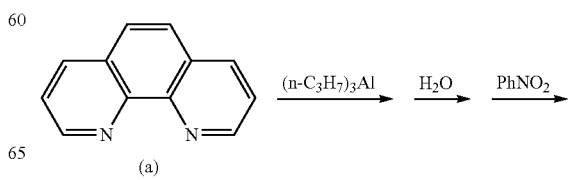

(a)

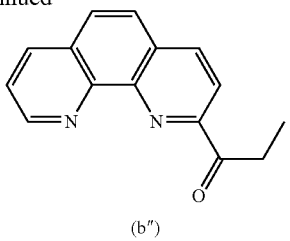

(b")

In order to prepare 2-n-propyl-acyl-1,10-phenanthroline as shown in Formula (b"), 1,10-phenanthroline is first reacted with (n-C$_3$H$_7$)$_3$Al in the presence of an organic solvent, which can be selected from toluene, cyclohexane, diethyl ether, tetrahydrofuran, ethanol, benzene, xylene, dichloromethane, mixtures thereof, etc., preferably toluene. A 1,10-phenanthroline solution with a concentration of 10 g/L to 200 g/L is prepared with the above organic solvents. The reaction between 1,10-phenanthroline and (n-C$_3$H$_7$)$_3$Al is commonly performed at a temperature in the range from −60° C. to −80° C., preferably from −60° C. to −70° C., favorably under protection of an inert gas, which is preferably selected as argon or nitrogen. Anhydrous or hydrous 1,10-phenanthroline, preferably anhydrous 1,10-phenanthroline, and (n-C$_3$H$_7$)$_3$Al per se are selected as the raw materials for the above reaction with a molar ratio of 1,10-phenanthroline to (n-C$_3$H$_7$)$_3$Al in the range from 1:0.5 to 1:4.5, preferably 1:2.0 to 1:2.6. Favorably, the reaction is carried out usually by adding, for example, dropwise adding (n-C$_3$H$_7$)$_3$Al at a reaction temperature into the 1,10-phenanthroline solution. After the above addition is completed, the resulting mixture is stirred for 18 h to 28 h at the reaction temperature, preferably 18 to 20 h. Afterwards, the reaction temperature is heated up to 20° C. to 40° C., before the resulting mixture is stirred again for 5 h to 10 h, preferably 10 h to facilitate more complete reaction. Next, water (preferably deionized water) is added for hydrolysis at a temperature in the range from −60° C. to 0° C. For example, water, preferably deionized water, can be added into the resulting mixture at −30° C. for hydrolysis. There are bubbles during hydrolysis process, and the hydrolysis process is not to be stopped until no bubbles come out. In order to ensure more complete hydrolysis, the resulting mixture is heated again to 20° C. to 40° C. and stirred for 5 h to 10 h. Subsequently, the resultant is separated and an organic phase therein is taken out. In order to obtain the required product as much as possible, an organic solvent is preferably used for extraction of the inorganic phase in the resultant, and then the organic phase is combined with the organic phase obtained through separation, wherein useful organic solvents can be ethyl acetate, acetone, dichloromethane, or a mixture thereof, preferably dichloromethane. The solvent is removed from the organic phase or combined organic phase under reduced pressure prior to addition of nitrobenzene therein for reflux (for example at 210° C.) for 10 h to 48 h, preferably 15 h to 24 h. After that, the resultant is filtered, and the solvent is removed under reduced pressure. A mixture solution of ethyl acetate and petroleum ether with a volume ratio therebetween in the range from 1:1 to 1:5, preferably 1:2 is used as an eluent to perform silica column chromatography to obtain a solid product, i.e., the compound as shown in Formula (b"). In the above synthesis step, the molar ratio of 1,10-phenanthroline to nitrobenzene is in the range from 1:0.5 to 1:30, preferably from 1:15 to 1:20.

Step b: synthesis of 2-n-propyl-acyl-1,10-phenanthroline aminal ligand: the compound as shown in Formula (b") is reacted with the compound as shown in Formula (c) in the presence of p-toluenesulfonic acid as the catalyst to obtain the compound as shown in Formula (d").

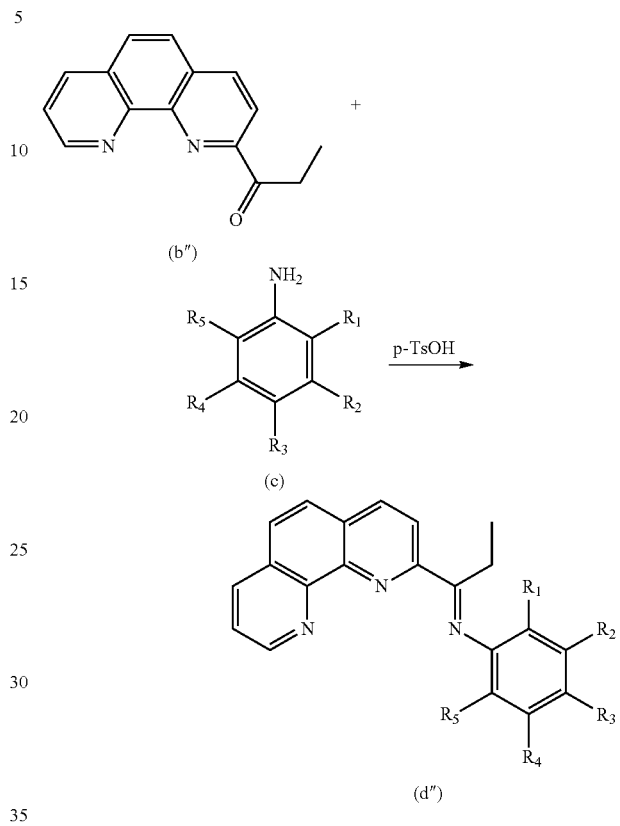

For definitions of R$_1$ to R$_5$, references can be made to definitions relating to Formula (III).

The product ligand as shown in Formula (d") is prepared by reacting 2-n-propyl-acyl-1,10-phenanthroline obtained in Step a with substituted anline as shown in Formula (c) in a container in the presence of an organic solvent containing no water or oxygen, wherein the molar ratio of 2-n-propyl-acyl-1,10-phenanthroline to substituted anline as shown in Formula (c) is in the range from 1:1 to 1:5. Said organic solvent can be selected from toluene, cyclohexane, diethyl ether, tetrahydrofuran, ethanol, benzene, xylene, dichloromethane, mixtures thereof, etc., preferably toluene. The reaction is carried out under reflux in the presence of p-toluenesulfonic acid (p-TsOH) as the catalyst at, for example 110° C., wherein the mass ratio of p-TsOH to the total amount of the reactants (i.e., the compounds as shown in Formulae (b") and (c)) is in the range from 0.001:1 to 0.02:1; and the reaction time is in the range from 5 h to 10 h. The reaction is monitored by TLC. Upon completion of the reaction of 2-n-propyl-acyl-1,10-phenanthroline, the solvent is removed under reduced pressure. After that, a mixture solution of ethyl acetate and petroleum ether with a volume ratio therebetween in the range from 1:1 to 1:9, preferably 1:4 is used as an eluent to perform silica column chromatography to obtain the target product, i.e., the compound as shown in Formula (d"). The target product is characterized by nuclear magnetism and mass spectrum.

Step c: synthesis of 2-n-propyl-acyl-1,10-phenanthroline aminal ferrous chloride complex: the compound as shown in Formula (d") is reacted with ferrous chloride to obtain the compound as shown in Formula (iii).

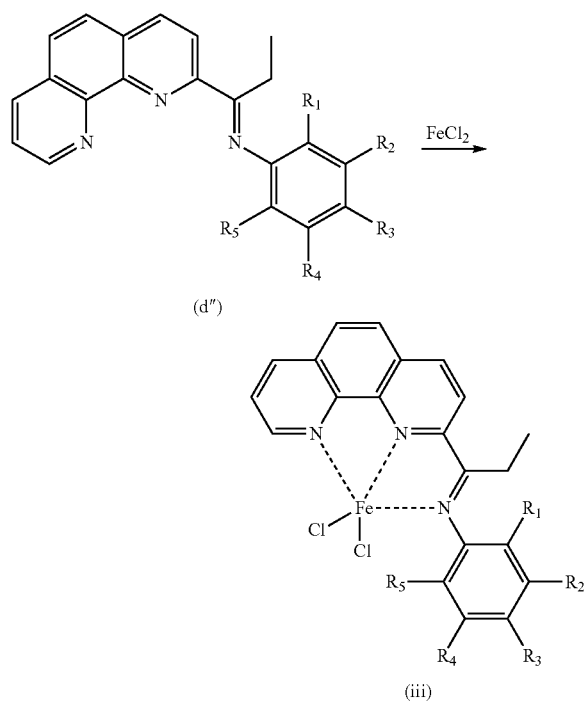

For definitions of $R_1$ to $R_5$, references can be made to definitions relating to Formula (III).

Under protection of an inert gas such as nitrogen, ferrous chloride is dissolved into an organic solvent containing no water or oxygen, so as to form a solution with a concentration of 0.001 g/ml to 0.1 g/ml, wherein the organic solvent can be selected from toluene, cyclohexane, diethyl ether, tetrahydrofuran, ethanol, benzene, xylene, dichloromethane, and mixtures thereof, preferably tetrahydrofuran. To obtain said ferrous chloride solution, hydrated ferrous chloride ($FeCl_2 \cdot 4H_2O$) can also be used instead of ferrous chloride. 2-n-propyl-acyl-1,10-phenanthroline ligand (d″) is separately dissolved into an organic solvent containing no water or oxygen to form a solution with a concentration of 0.01 g/ml to 0.1 g/ml, wherein the organic solvent can be selected from toluene, cyclohexane, diethyl ether, tetrahydrofuran, ethanol, benzene, xylene, dichloromethane, and mixtures thereof, preferably tetrahydrofuran. Subsequently, the above two solutions are combined (for example at room temperature) under protection of an inner gas such as nitrogen, and the resulting mixture is stirred for some time under protection of an inert gas such as nitrogen, for example, being stirred overnight at room temperature. The reaction is monitored by TLC. Upon completion of the reaction, conventional treatment methods of suction filtration, washing, drying, etc. are adopted to treat the reaction product to obtain the compound ligand as shown in Formula (iii). Said washing can be performed using an organic solvent such as anhydrous diethyl ether. The ligand is characterized by elemental analysis and infrared spectroscopy. In the synthesis step, the molar ratio of 2-n-propyl-acyl-1,10-phenanthroline ligand (d″) to ferrous chloride is in the range from 1:1 to 1.2:1, preferably from 1.05:1 to 1.1:1.

According to another aspect of the present disclosure, it provides a process for ethylene oligomerization. Ethylene is oligomerized in the presence of the above catalyst composition, which comprises imino ferrous complex shown in Formula (I) as the main catalyst, an aluminum-containing cocatalyst, water, and an organic solvent.

In the oligomerization process according to the present disclosure, preferably, based on weight of the organic solvent, the catalyst composition has a content of water in the range from 5 to 450 ppm, preferably from 5 to 350 ppm, more preferably 20 to 260 ppm, and further preferably from 50 to 200 ppm.

In the catalyst composition used for ethylene oligomerization of the present disclosure, imino ferrous complex shown in Formula (I) as previously defined is adopted as the main catalyst.

In one specific embodiment, the mixing of the main catalyst and cocatalyst is performed in an atmosphere of ethylene (i.e., the main catalyst and cocatalyst are mixed in the presence of ethylene). In a specific embodiment, the reaction temperature can be in the range from −20° C. to 150° C., preferably from 0° C. to 80° C., and more preferably from 5° C. to 35° C. In another specific embodiment, when the compound as shown in Formula (vii) which contains a pyridyl group is used, the reaction temperature can be in the range from −20° C. to 150° C., preferably from 0° C. to 80° C., and more preferably from 5° C. to 50° C. In the present disclosure, the reaction pressure can be selected as 0.1 MPa to 30 MPa. Generally, the oligomerization activity improves as the pressure of ethylene increases.

In the ethylene oligomerization process according to the present disclosure, preferred ranges of varieties of organic solvents, varieties of cocatalysts, content of the main catalyst in view of the organic solvents, molar ratio of the cocatalysts to the main catalyst are correspondingly the same as those concerning the catalyst composition for ethylene oligomerization of the present disclosure.

According to the present disclosure, one specific embodiment of the process of ethylene oligomerization can comprise the following steps. (1) The reaction system is replaced through operations such as high temperature drying, vacuum replacement, etc., so as to ensure an anhydrous and oxygen-free reaction system. (2) The reaction system is replaced with ethylene, so as to ensure an ethylene atmosphere for the reaction system. (3) The catalyst composition including the main catalyst, the cocatalyst, water, and the organic solvent is added in the reaction system, followed by adequate stirring. (4) Ethylene is fed into the system to perform the oligomerization reaction, which is kept for 30 min to 100 min under 0.1 MPa to 30 MPa at −20° C. to 150° C. (5) The reaction is stopped and the product is analyzed by gas chromatography (GC). In the present disclosure, in step (3), the main catalyst and cocatalyst can be added into the system after being dissolved into the organic solvent.

When the catalyst composition according to the present disclosure is used for ethylene oligomerization, products obtained therein include $C_4$, $C_6$, $C_8$, $C_{10}$, $C_{12}$, $C_{14}$, $C_{16}$, $C_{18}$, $C_{20}$, $C_{22}$, etc., with selectivity of α-olefins thereof higher than 96%. When the ethylene oligomerization is completed, the products are analyzed by GC. Results indicate that the oligomerization activity can be higher than $10^7$ g·mol $(Fe)^{-1} \cdot h^{-1}$. Furthermore, when the remaining reaction mixture is neutralized by an ethanol solution acidified with dilute hydrochloric acid, no polymers can be obtained.

Compared to an anhydrous catalyst composition system, when the catalyst composition according to the present disclosure comprising imino ferrous complex shown in Formula (I) as the main catalyst, the aluminum-containing cocatalyst, water, and the organic solvent is used in ethylene oligomerization, a higher oligomerization activity can be acquired, with high selectivity of α-olefins, and rapid initiation, stable operation, and good repeatability of the reaction. According to the present disclosure, a rather low ratio of Al/Fe or a low reaction temperature can still enable a high oligomerization activity. The present disclosure overcomes technical prejudices of persons skilled in the art and achieves unexpected technical effects.

EXAMPLES

The present disclosure will be further explained in connection with specific examples, which, however, are not to limit the present disclosure in any manner.

Example 1

2-formyl-1,10-phenanthroline (2,6-diethylanil) $FeCl_2$ is used as the main catalyst.

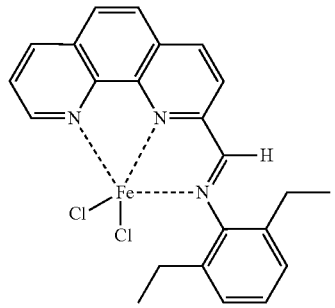

It comprises the following specific steps in using the catalyst composition for ethylene oligomerization. (1) The reaction system is replaced through operations such as high temperature drying, vacuum replacement, etc., so as to ensure an anhydrous and oxygen-free reaction system. (2) The reaction system is replaced with ethylene, so as to ensure an ethylene atmosphere in the reaction system. (3) A reaction kettle is added with a certain amount of hydrous toluene, 1.37 ml of a toluene solution of $Et_3Al$ (with a concentration of 715 μmol/ml), and 2 ml of a toluene solution of 2-formyl-1,10-phenanthroline (2,6-diethylanil) $FeCl_2$ (with a concentration of 2.5 μmol/ml). As a result, the total amount of the composition is 100 ml. The content of water based on weight of the organic solvent is 5 ppm, and the ratio of Al/Fe is 196. After adequate stirring, ethylene is fed into the kettle to perform the oligomerization reaction. (4) The oligomerization reaction is kept for 30 min under an ethylene pressure of 1 MPa at 30° C. (5) The reaction is stopped, and a small amount of reaction product is taken out for gas chromatography (GC) analysis.

In this example, the activity of the catalyst for catalyzing the ethylene oligomerization is $0.51 \times 10^7$ g·mol(Fe)$^{-1}$·h$^{-1}$. The oligomers contain 22.3% of $C_4$, 46.22% of $C_6$ to $C_{10}$, 70.32% (wherein α-olefins account for 97.8%) of $C_6$ to $C_{18}$, and 7.38% of $C_{20}$ to $C_{28}$. The remaining mixture is neutralized by an ethanol solution acidified with dilute hydrochloric acid of 5%, and no polymers are obtained. The analysis results are shown in Table 1.

Examples 2 to 12

The steps in Example 1 are repeated only with different contents of water and reaction parameters. The data are shown in Table 1.

Comparative Example 1

The steps of Example 1 are repeated only with 0 ppm of water. The data are shown in Table 1.

TABLE 1

| | Content of water (ppm) | T (° C.) | Al/Fe (mol) | Activity ($10^7$ g·mol (Fe)$^{-1}$·h$^{-1}$) | $C_4$ (%) | $C_6$~$C_{10}$ (%) | $C_6$~$C_{18}$ Content (%) | $C_6$~$C_{18}$ Linear α-olefins (%) | $C_{20}$~$C_{28}$ (%) |
|---|---|---|---|---|---|---|---|---|---|
| Example 1 | 5 | 30 | 196 | 0.51 | 22.3 | 46.22 | 70.32 | 97.8 | 7.38 |
| Example 2 | 20 | 30 | 196 | 0.72 | 25.24 | 47.77 | 69.04 | 97.6 | 5.72 |
| Example 3 | 50 | 30 | 196 | 1.11 | 25.13 | 49.01 | 69.76 | 97.7 | 5.11 |
| Example 4 | 120 | 30 | 196 | 1.18 | 26.04 | 48.04 | 68.79 | 97.6 | 5.17 |
| Example 5 | 200 | 30 | 196 | 1.2 | 23.71 | 48.08 | 69.76 | 97.9 | 6.53 |
| Example 6 | 260 | 30 | 196 | 0.8 | 25.86 | 48.16 | 68.65 | 98.2 | 5.49 |
| Example 7 | 350 | 30 | 196 | 0.55 | 25.75 | 48.23 | 69.15 | 97.4 | 5.1 |
| Example 8 | 200 | 0 | 196 | 1.09 | 27.91 | 48.19 | 67.61 | 97.1 | 4.48 |
| Example 9 | 200 | −10 | 196 | 0.96 | 26.41 | 45.76 | 67.88 | 97.9 | 5.71 |
| Example 10 | 200 | −20 | 196 | 0.94 | 28.3 | 48.12 | 66.92 | 97.5 | 4.78 |
| Example 11 | 200 | 50 | 196 | 0.61 | 30.25 | 47.59 | 66.03 | 98.1 | 3.72 |
| Example 12 | 200 | 30 | 500 | 1.32 | 31.7 | 49.19 | 65.52 | 96.2 | 2.78 |
| Comparative Example 1 | 0 | 30 | 196 | 0.2 | 27.81 | 45.83 | 66.69 | 98 | 5.5 |

The data in Table 1 indicate that a high ethylene oligomerization activity is obtained in the presence of the catalyst composition according to the present disclosure which contains water. More specifically, from comparisons between catalyst activity in Examples 1 to 7 to that in Comparative Example 1, it can be obvious seen that, under the same oligomerization conditions, the activity of the catalyst composition according to the present disclosure is 2.5 to 6 times of that of the catalyst used in Comparative Example 1. Furthermore, the examples according to the present disclosure obtain as high a selectivity of α-olefins as Comparative Example 1 does. Particularly, in Examples 3 to 5, when the content of water ranges from 50 ppm to 200 ppm, the ethylene oligomerization activity exceeds $1 \times 10^7$ g·mol(Fe)$^{-1}$·h$^{-1}$. It is thus clear that the catalyst having a content of water within the above range is especially suitable for catalyzing ethylene oligomerization in industrial production. In addition, the oligomerization reaction according to the present disclosure is of rapid initiation, stable operation, and good repeatability.

Moreover, Table 1 shows that even when the ratio of Al to Fe is as low as 196, the catalyst of the present disclosure still has good activity for catalyzing the oligomerization reaction, thereby significantly reducing costs of ethylene oligomerization. Hence, the catalyst according to the present disclosure is of high practicability and has broad prospects for industrialization. Besides, Examples 5, 8, 9, and 10 prove that, according to the present disclosure, high oligomerization activity can still be obtained even at a low reaction temperature.

Example 13

1. Synthesis of a complex of 2-acetyl-1,10-phenanthroline (2,6-diethylanil) FeCl$_2$ a) Synthesis of 2-acetyl-1,10-phenanthroline (See the Following Reaction Procedure)

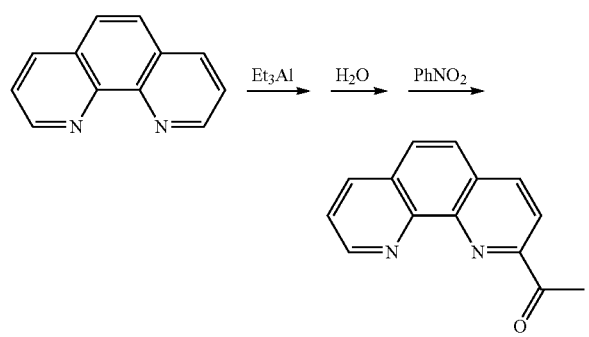

5.1 g (28.3 mmol) of 1,10-phenanthroline is put into a 250 ml, three-necked flask, and is dissolved into 100 ml of toluene under protection of nitrogen and magnetic stirring. 10 ml (70.8 mmol) of Et$_3$Al is dropwise added into the three-necked flask under stirring at −60° C. in about 15 min, and the resulting mixture is stirred at the same temperature for 18 h. Afterwards, the resulting mixture is heated to about 30° C. and stirred for another 10 h. Next, the reaction mixture is cooled down to about −30° C. followed by slow addition of 50 ml of distilled water. Then the mixture is heated again to 30° C. and stirred for 10 h. Subsequently, liquid separation is performed and an organic phase is taken out. An inorganic phase is extracted with dichloromethane for three times, each time with an amount of 20 ml of dichloromethane. The organic phases are combined. The solvent is removed under reduced pressure. Afterwards, 50 ml (1.205 g/ml) of nitrobenzene is added and refluxed for about 18 h at 210° C. After filtration, the nitrobenzene is removed under distillation at a pressure lower than 10 mmHg to obtain a black viscous liquid substance. A mixture solution of ethyl acetate and petroleum ether with a volume ratio of 1:2 is used as an eluent to perform silica column chromatography to the obtained black viscous liquid substance, so as to obtain a brown product, which weighs 1.9 g with a yield of 30%. The product, after nuclear magnetic resonance analysis and mass spectrometry, is determined as the compound as referred to under a), i.e., 2-acetyl-1,10-phenanthroline.

Mass spectrometry MS-EI: 222.

Nuclear magnetic resonance analysis: $^1$H NMR (300 MHz, CDCl$_3$): δ9.26 (d, J=3.9 Hz, 1 H); 8.37 (s, 2 H); 8.29 (d, J=8.1 Hz, 1 H); 8.7 (dd, J=8.7 Hz, 2 H); 7.69 (dd, J=7.8 Hz, 1 H); 3.09 (s, 3 H, CH$_3$).

b) Synthesis of 2-acetyl-1,10-phenanthroline (2,6-diethylanil) Ligand (See the Following Reaction Procedure)

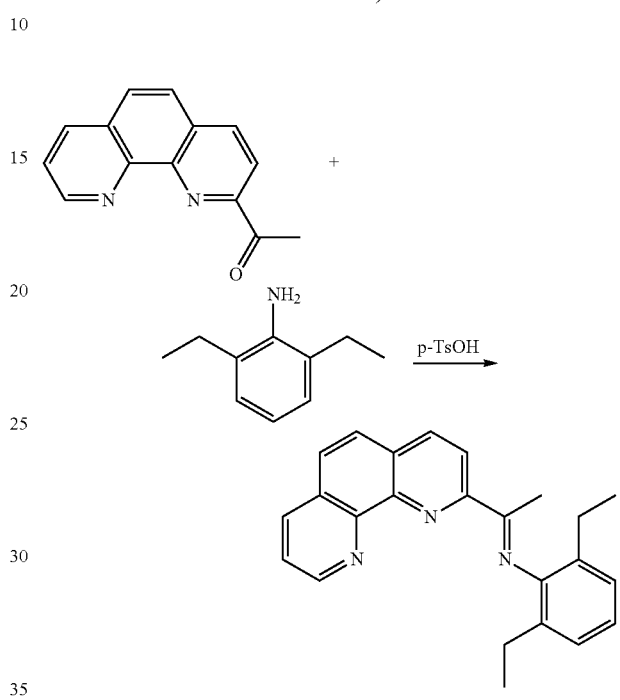

0.47 g (2.12 mmol) of 2-acetyl-1,10-phenanthroline obtained in step a), 0.95 g (6.36 mmol) of 2,6-diethylaniline with a molar ratio of 1:3, and 35 ml of toluene containing no water or oxygen are put into a 100 ml, two-necked flask having a manifold. The manifold is provided with a condenser pipe. 0.01 g of p-toluene sulfonic acid is added and refluxed at 110° C. After 6 h of reaction, the solvent is removed under reduced pressure. A mixture solution of ethyl acetate and petroleum ether with a volume ratio of 1:4 is used as an eluent to perform silica column chromatography to obtain a bright yellow product, which weighs 0.61 g with a yield of 81%. The product, after nuclear magnetic resonance analysis, mass spectrometry, and elemental analysis, is determined as the compound as referred to under b), i.e., 2-acetyl-1,10-phenanthroline (2,6-diethylanil).

Mass spectrometry MS-EI: 353.

Nuclear magnetic resonance analysis: $^1$H NMR (300 MHz, CDCl$_3$); δ9.25 (dd, J=3.0 Hz, 1 H); 8.80 (d, J=8.3 Hz, 1 H); 8.35 (d, J=8.3 Hz, 1 H); 8.27 (dd, J=7.8 Hz, 1 H, 7.86 (s, 2 H); 7.66 (m, 1 H); 7.15 (d, J=7.6 Hz, 2 H, 6.96 (t, J=7.5 Hz, 1 H); 2.58 (s, 3 H, CH$_3$); 2.43 (m, 4 H, CH$_2$CH$_3$), 1.16 (t, J=7.5 Hz, 6 H, CH$_2$CH$_3$).

$^{13}$C NMR (75 MHz, CDCl$_3$); δ167.8, 156.2, 150.7, 148.0, 146.4, 145.2, 136.5, 131.1, 129.5, 129.0, 127.5, 126.5, 126.0, 123.4, 122.9, 120.8, 24.6, 17.3, 13.7.

Elemental analysis: C$_{24}$H$_{23}$N$_3$ (353.46). Theoretical value: C, 81.55; H, 6.56; N, 11.89. Measured value: C, 80.88; H, 6.59; N, 11.78.

c) Synthesis of 2-acetyl-1,10-phenanthroline (2,6-diethylanil) FeCl$_2$ (See the Following Reaction Procedure)

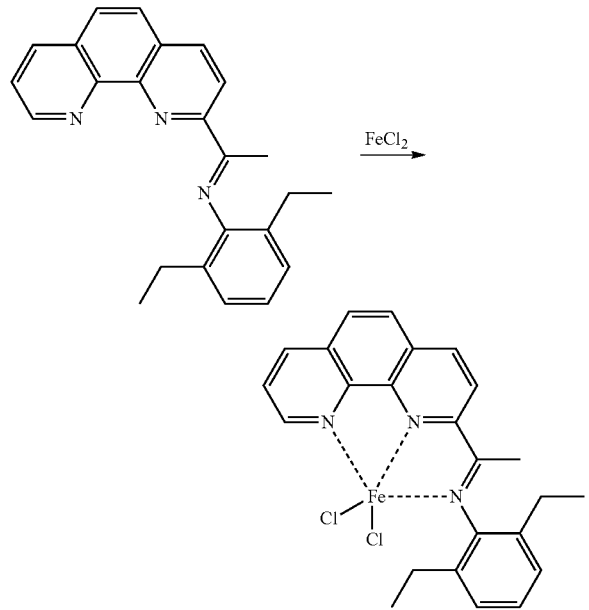

Under protection of nitrogen, 0.16 g (1.25 mmol) of FeCl$_2$ is dissolved into 20 ml of tetrahydrofuran containing no water or oxygen in a two-necked flask. 0.48 g (1.36 mmol) of 2-acetyl-1,10-phenanthroline (2,6-diethylanil) obtained in step b) is separately dissolved into 20 ml of tetrahydrofuran containing no water or oxygen. The above two solutions are then combined under protection of nitrogen at room temperature. The reaction occurs immediately and the solution takes on the color of ash black. The resultant is stirred overnight under protection of nitrogen at room temperature. The reaction is monitored by TLC until the 2-acetyl-1,10-phenanthroline (2,6-diethylanil) ligand substantially disappears. After suction filtration and washing with anhydrous diethyl ether, vacuum drying is performed to obtain a silver gray solid. The obtained solid is determined as the compound as referred to under c), i.e., 2-acetyl-1,10-phenanthroline (2,6-diethylanil) FeCl$_2$, the elemental analysis of which is as follows.

Elemental analysis: $C_{24}H_{23}Cl_2FeN_3$ (480.22). Theoretical value: C, 60.09; H, 4.90; N, 8.76. Measured value: C, 60.03; H, 4.83; N, 8.75.

2. The ethylene oligomerization process comprises the following specific steps. (1) The reaction system is replaced through operations such as high temperature drying, vacuum replacement, etc., so as to ensure an anhydrous and oxygen-free reaction system. (2) The reaction system is replaced with ethylene, so as to ensure an ethylene atmosphere in the reaction system. (3) A reaction kettle is added with of water and toluene as solvents, 1.37 ml of a toluene solution of Et$_3$Al (with a concentration of 715 μmol/ml), and 2 ml of a toluene solution of 2-acetyl-1,10-phenanthroline (2,6-diethylanil) FeCl$_2$ (with a concentration of 2.5 μmol/ml). As a result, the total amount of the composition is 100 ml, wherein based on weight of the organic solvent (i.e., toluene), the content of water is 5 ppm, and the ratio of Al/Fe is 196. After adequate stirring, ethylene is fed into the kettle to perform the oligomerization reaction. (4) The oligomerization reaction is kept for 30 min under an ethylene pressure of 1 MPa at 30° C. (5) The reaction is stopped, and a small amount of reaction product is taken out for gas chromatography (GC) analysis. The oligomerization activity is $0.68 \times 10^7$ g·mol(Fe)$^{-1}$·$^{-1}$. The oligomers contain 28.21% of $C_4$, 56.41% of $C_6$ to $C_{10}$, 69.77% (wherein α-olefins account for 98.1%) of $C_6$ to $C_{18}$, and 2.01% of $C_{20}$ to $C_{28}$. The remaining mixture is neutralized by an ethanol solution acidified with dilute hydrochloric acid of 5%, and no polymers are obtained. The analysis results are shown in Table 2.

Examples 14 to 24

The steps in Example 13 are repeated only with different contents of water and reaction parameters. The data are shown in Table 2.

Comparative Example 2

The steps of Example 13 are repeated only with 0 ppm of water. The data are shown in Table 2.

TABLE 2

| Number | Content of water (ppm) | T (° C.) | Al/Fe (mol) | Activity ($10^7$ g·mol (Fe)$^{-1}$·h$^{-1}$) | $C_4$ (%) | $C_6$~$C_{10}$ (%) | $C_6$~$C_{18}$ Content (%) | Linear α-olefins (%) | $C_{20}$~$C_{28}$ (%) |
|---|---|---|---|---|---|---|---|---|---|
| Example 13 | 5 | 30 | 196 | 0.68 | 28.21 | 56.14 | 69.77 | 98.1 | 2.01 |
| Example 14 | 20 | 30 | 196 | 0.89 | 27.90 | 55.84 | 69.93 | 98.2 | 2.17 |
| Example 15 | 50 | 30 | 196 | 1.35 | 21.96 | 50.48 | 72.72 | 97.9 | 5.32 |
| Example 16 | 120 | 30 | 196 | 1.28 | 22.02 | 53.55 | 74.24 | 97.5 | 3.74 |
| Example 17 | 200 | 30 | 196 | 1.37 | 22.99 | 49.50 | 71.81 | 97.6 | 5.20 |
| Example 18 | 260 | 30 | 196 | 0.97 | 24.03 | 49.33 | 71.09 | 97.8 | 4.88 |
| Example 19 | 350 | 30 | 196 | 0.72 | 30.88 | 56.95 | 67.53 | 96.8 | 1.59 |
| Example 20 | 200 | 0 | 196 | 1.26 | 23.71 | 50.20 | 71.51 | 97.6 | 4.77 |
| Example 21 | 200 | −10 | 196 | 1.13 | 21.45 | 49.56 | 72.89 | 97.7 | 5.66 |
| Example 22 | 200 | −20 | 196 | 1.11 | 22.62 | 46.62 | 71.27 | 97.8 | 6.11 |
| Example 23 | 200 | 50 | 196 | 0.78 | 25.75 | 48.23 | 69.15 | 97.4 | 5.10 |
| Example 24 | 200 | 30 | 500 | 1.49 | 26.93 | 50.31 | 69.20 | 98.4 | 3.87 |
| Comparative Example 2 | 0 | 30 | 196 | 0.43 | 27.29 | 51.04 | 69.32 | 95.3 | 3.39 |

The data in Table 2 indicate that a high ethylene oligomerization activity is obtained in the presence of the catalyst composition according to the present disclosure which comprises the main catalyst, i.e., the 2-acetyl-1,10-phenanthroline (anil) $FeCl_2$ complex, the aluminum-containing cocatalyst, water, and the organic solvent. Moreover, high selectivity of α-olefins, and rapid initiation, stable operation, and good repeatability of the oligomerization reaction can be obtained. Particularly, When the content of water ranges from 50 ppm to 200 ppm, the ethylene to oligomerization activity exceeds $1\times10^7$ g·mol(Fe)$^{-1}$.h$^{-1}$. It is thus clear that the catalyst having a content of water within the above range is especially suitable for catalyzing ethylene oligomerization in industrial production. Moreover, even when the ratio of Al to Fe is rather low, a good oligomerization activity can still be obtained. In addition, according to the present disclosure, high oligomerization activity can still be obtained at a low reaction temperature.

Example 25

1. Synthesis of a complex of 2-n-propyl-acyl-1,10-phenanthroline (2,6-diethylanil) $FeCl_2$ a) Synthesis of 2-n-propyl-acyl-1,10-phenanthroline 5.1 g (28.3 mmol) of 1,10-phenanthroline is put into a 250 ml, three-necked flask, and is dissolved into 100 ml of toluene under protection of nitrogen and magnetic stirring. 13.5 ml (d=0.82 g/ml, 70.9 mmol) of (n-$C_3H_7$)$_3$Al is dropwise added into the three-necked flask under stirring at −60° C. in about 15 min, and the resulting mixture is stirred at the same temperature for 18 h. Afterwards, the resulting mixture is heated to about 30° C. and stirred for another 10 h. Next, the reaction mixture is cooled down to about −30° C. followed by slow addition of 50 ml of distilled water. Then the mixture is heated again to 30° C. and stirred for 10 h. Subsequently, liquid separation is performed and an organic phase is taken out. An inorganic phase is extracted with dichloromethane for three times, each time with an amount of 20 ml of dichloromethane. The organic phases are combined. The solvent is removed under reduced pressure. Afterwards, 50 ml (1.205 g/ml) of nitrobenzene is added and refluxed for about 18 h at 210° C. After filtration, the nitrobenzene is removed under distillation at a pressure lower than 10 mmHg to obtain a black viscous liquid substance. A mixture solution of ethyl acetate and petroleum ether with a volume ratio of 1:2 is used as an eluent to perform silica column chromatography to the obtained black viscous liquid substance, so as to obtain a brown product, which weighs 2.0 g with a yield of 30%. The product, after nuclear magnetic resonance analysis and mass spectrometry, is determined as the compound as referred to under a), i.e., 2-n-propyl-acyl-1,10-phenanthroline.

Mass spectrometry MS-EI: 236.

Nuclear magnetic resonance analysis: $^1$H NMR (400 MHz, $CDCl_3$): δ9.26 (dd, J=1.72, 1 H); 8.33 (s, 2 H); 8.27 (dd, J=1.68, 1 H); 7.86 (d, J=8.8, 1 H); 7.80 (d, J=8.8, 1H); 7.68 (dd, J=5.28, 1 H); 3.67 (m, J=7.24, 2 H); 1.10 (t, J=7.4, 3 H).

b) Synthesis of 2-n-propyl-acyl-1,10-phenanthroline (2,6-diethylanil) Ligand 0.50 g (2.12 mmol) of 2-n-propyl-acyl-1,10-phenanthroline obtained in step a), 0.95 g (6.36 mmol) of 2,6-diethylaniline with a molar ratio of 1:3, and 35 ml of toluene containing no water or oxygen are put into a 100 ml, two-necked flask having a manifold. The manifold is provided with a condenser pipe. 0.01 g of p-toluene sulfonic acid is added and refluxed at 110° C. After 6 h of reaction, the solvent is removed under reduced pressure. A mixture solution of ethyl acetate and petroleum ether with a volume ratio of 1:4 is used as an eluent to perform silica column chromatography to obtain a bright yellow product, which weighs 0.63 g with a yield of 81%. The product, after nuclear magnetic resonance analysis, mass spectrometry, and elemental analysis, is determined as the compound as referred to under b)), i.e., 2-n-propyl-acyl-1,10-phenanthroline (2,6-diethylanil).

Mass spectrometry MS-EI: 367.

Nuclear magnetic resonance analysis: $^1$H NMR (400 MHz, $CDCl_3$): δ9.25 (dd, J=2.96, 1 H); 8.66 (d, J=8.36, 1 H); 8.33 (d, J=8.36, 1H); 8.28 (dd, J=7.84, 1H); 7.85 (dd, J=9.02, 2H); 7.65 (dd, J=4.36, 1 H); 7.15 (d, J=7.52, 2H); 7.06 (t, J=7.04, 1H); 3.01 (t, J=7.84, —$CNCH_2CH_3$, 2 H), 2.40 (m, J=7.52, ph$CH_2CH_3$, 2 H); 1.20 (t, J=7.30, ph$CH_2CH_3$, 6 H); 0.90 (t, J=7.32, $CH_3CH_2CN$, 3 H).

Elemental analysis: $C_{25}H_{25}N_3$ (367.49). Theoretical value: C, 81.71; H, 6.86; N, 11.43. Measured value: C, 81.66; H, 6.87; N, 11.47.

c) Synthesis of 2-n-propyl-acyl-1,10-phenanthroline (2,6-diethylanil) $FeCl_2$

Under protection of nitrogen, 0.16 g (1.25 mmol) of $FeCl_2$ is dissolved into 20 ml of tetrahydrofuran containing no water or oxygen in a two-necked flask. 0.50 g (1.36 mmol) of 2-n-propyl-acyl-1,10-phenanthroline (2,6-diethylanil) obtained in step b) is separately dissolved into 20 ml of tetrahydrofuran containing no water or oxygen. The above two solutions are then combined under protection of nitrogen at room temperature. The reaction occurs immediately and the solution takes on the color of ash black. The resultant is stirred overnight under protection of nitrogen at room temperature. The reaction is monitored by TLC until the 2-n-propyl-acyl-1,10-phenanthroline (2,6-diethylanil) ligand substantially disappears. After suction filtration and washing with anhydrous diethyl ether, vacuum drying is performed to obtain a silver gray solid. The obtained solid is determined as the compound as referred to under c), i.e., 2-n-propyl-acyl-1,10-phenanthroline (2,6-diethylanil) $FeCl_2$, the elemental analysis of which is as follows.

Elemental analysis: $C_{25}H_{25}Cl_2FeN_3$ (494.24). Theoretical value: C, 60.75; H, 5.10; N, 8.50. Measured value: C, 60.71; II, 5.00; N, 8.53.

2. Ethylene Oligomerization

A stainless steel autoclave is added with toluene, water, 1.37 ml of a toluene solution of $Et_3Al$ (with a concentration of 715 μmol/ml) as the cocatalyst, and 2 ml of a toluene solution of 2-n-propyl-acyl-1,10-phenanthroline (2,6-diethylanil) $FeCl_2$ (with a concentration of 2.5 μmol/ml) as the main catalyst. As a result, the total amount of the composition is 100 ml, wherein the ratio of Al/Fe is 196, and based on weight of toluene, the content of water is 5 ppm. When the oligomerization temperature reaches 30° C., ethylene is fed into the autoclave. The reaction is kept for 30 min under stirring and an ethylene pressure of 1 MPa. A small amount of reaction product is taken out for GC analysis. The oligomerization activity is $0.57\times10^7$ g·mol(Fe)$^{-1}$.h$^{-1}$. The oligomers contain 12.92% of $C_4$, 42.13% of $C_6$ to $C_{10}$, 73.32% (wherein α-olefins account for 97.6%) of $C_6$ to $C_{18}$, and 13.76% of $C_{20}$ to $C_{28}$. The value of K is 0.63. The remaining mixture is neutralized by an ethanol solution acidified with dilute hydrochloric acid of 5%, and no polymers are obtained. The analysis results are shown in Table 3.

Examples 26 to 36

The steps in Example 25 are repeated only with different contents of water and reaction parameters. The data are shown in Table 3.

Comparative Example 3

The steps of Example 25 are repeated only with 0 ppm of water. The data are shown in Table 3.

TABLE 3

| Number | Content of water (ppm) | T (° C.) | Al/Fe (mol) | Activity ($10^7$ g·mol$^{-1}$·h$^{-1}$) | $C_4$ (%) | $C_6$~$C_{10}$ (%) | $C_6$~$C_{18}$ Content (%) | Linear α-olefins (%) | $C_{20}$~$C_{28}$ (%) |
|---|---|---|---|---|---|---|---|---|---|
| Example 25 | 5 | 30 | 196 | 0.57 | 12.92 | 42.13 | 73.32 | 97.6 | 13.76 |
| Example 26 | 20 | 30 | 196 | 0.68 | 10.27 | 36.99 | 67.18 | 97.6 | 22.55 |
| Example 27 | 50 | 30 | 196 | 1.04 | 9.82 | 35.34 | 66.56 | 97.8 | 23.62 |
| Example 28 | 120 | 30 | 196 | 0.97 | 9.52 | 36.99 | 67.18 | 96.2 | 21.73 |
| Example 29 | 200 | 30 | 196 | 1.06 | 9.85 | 37.81 | 68.31 | 97.6 | 21.84 |
| Example 30 | 260 | 30 | 196 | 0.66 | 9.4 | 35.72 | 67.49 | 97.5 | 23.1 |
| Example 31 | 350 | 30 | 196 | 0.51 | 8.06 | 29.35 | 58.47 | 96.1 | 33.47 |
| Example 32 | 200 | 0 | 196 | 0.95 | 9.79 | 37.43 | 69.47 | 96.8 | 20.74 |
| Example 33 | 200 | −10 | 196 | 0.82 | 11.35 | 40.37 | 73.25 | 97.8 | 15.4 |
| Example 34 | 200 | −20 | 196 | 0.8 | 11.64 | 35.39 | 65.27 | 97.8 | 23.09 |
| Example 35 | 200 | 50 | 196 | 0.67 | 11.91 | 43.14 | 70.02 | 97.7 | 14.96 |
| Example 36 | 200 | 30 | 500 | 1.18 | 8.38 | 34.02 | 65 | 98 | 26.63 |
| Comparative Example 3 | 0 | 30 | 196 | 0.44 | 27.25 | 51.14 | 69.52 | 95.5 | 3.42 |

The data in Table 3 indicate that a high ethylene oligomerization activity is obtained in the presence of the catalyst composition according to the present disclosure which comprises the main catalyst, i.e., the complex of 2-n-propyl-acyl-1,10-phenanthroline (anil) FeCl$_2$, the aluminum-containing cocatalyst (such as Et$_3$Al), water, and the organic solvent. Moreover, high selectivity of α-olefins can be obtained. Besides, even when the ratio of Al to Fe is rather low, the catalyst of the present disclosure still possesses good oligomerization activity, and high oligomerization activity can still be obtained at a low reaction temperature. Particularly, when the content of water ranges from 50 ppm to 200 ppm, the ethylene oligomerization activity approaches or exceeds 1×10$^7$ g·mol(Fe)$^{-1}$·h$^{-1}$. It is thus clear that the catalyst having a content of water within the above range is especially suitable for catalyzing ethylene oligomerization in industrial production.

Example 37

2-butyryl-1,10-phenanthroline (2,6-diethylanil) FeCl$_2$ is used as the main catalyst.

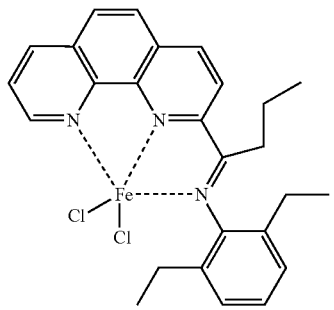

It comprises the following specific steps in using the catalyst composition for ethylene oligomerization. (1) The reaction system is replaced through operations such as high temperature drying, vacuum replacement, etc., so as to ensure an anhydrous and oxygen-free reaction system. (2) The reaction system is replaced with ethylene, so as to ensure an ethylene atmosphere in the reaction system. (3) A reaction kettle is added with a certain amount of hydrous toluene, 1.37 ml of a toluene solution of Et$_3$Al (with a concentration of 715 μmol/ml), and 2 ml of a toluene solution of 2-butyryl-1,10-phenanthroline (2,6-diethylanil) FeCl$_2$ (with a concentration of 2.5 μmol/ml). As a result, the total amount of the composition is 100 ml. The content of water based on weight of the organic solvent is 5 ppm, and the ratio of Al/Fe is 196. After adequate stirring, ethylene is fed into the kettle to perform the oligomerization reaction. (4) The oligomerization reaction is kept for 30 min under an ethylene pressure of 1 MPa at 30° C. (5) The reaction is stopped, and a small amount of reaction product is taken out for gas chromatography (GC) analysis.

In this example, the activity of the catalyst for catalyzing the ethylene oligomerization is 0.57×10$^7$ g·mol(Fe)$^{-1}$·h$^{-1}$. The oligomers contain 40.66% of C$_4$, 47.77% of C$_6$ to C$_{10}$, 58.25% (wherein α-olefins account for 97.2%) of C$_6$ to C$_{18}$, and 1.09% of C$_{20}$ to C$_{28}$. The remaining mixture is neutralized by an ethanol solution acidified with dilute hydrochloric acid of 5%, and no polymers are obtained. The analysis results are shown in Table 4.

Examples 38 to 48

The steps in Example 37 are repeated only with different contents of water and reaction parameters. The data are shown in Table 4.

Comparative Example 4

The steps of Example 37 are repeated only with 0 ppm of water. The data are shown in Table 4.

TABLE 4

| | Content of water (ppm) | T (° C.) | Al/Fe (mol) | Activity ($10^7$ g·mol (Fe)$^{-1}$·h$^{-1}$) | $C_4$ (%) | $C_6$~$C_{10}$ (%) | $C_6$~$C_{18}$ Content (%) | Linear α-olefins (%) | $C_{20}$~$C_{28}$ (%) |
|---|---|---|---|---|---|---|---|---|---|
| Example 37 | 5 | 30 | 196 | 0.57 | 40.66 | 47.77 | 58.25 | 97.2 | 1.09 |
| Example 38 | 20 | 30 | 196 | 0.78 | 46.68 | 36.50 | 50.32 | 97.2 | 3.00 |
| Example 39 | 50 | 30 | 196 | 1.24 | 43.92 | 36.77 | 52.41 | 98.1 | 3.68 |
| Example 40 | 120 | 30 | 196 | 1.17 | 31.73 | 47.22 | 64.97 | 97.7 | 3.31 |

TABLE 4-continued

|  | Content of water (ppm) | T (° C.) | Al/Fe (mol) | Activity ($10^7$ g · mol $(Fe)^{-1} \cdot h^{-1}$) | $C_4$ (%) | $C_6\text{~}C_{10}$ (%) | $C_6\text{~}C_{18}$ Content (%) | Linear α-olefins (%) | $C_{20}\text{~}C_{28}$ (%) |
|---|---|---|---|---|---|---|---|---|---|
| Example 41 | 200 | 30 | 196 | 1.26 | 30.85 | 43.91 | 60.24 | 96.0 | 8.91 |
| Example 42 | 260 | 30 | 196 | 0.86 | 34.31 | 44.12 | 61.42 | 96.7 | 4.26 |
| Example 43 | 350 | 30 | 196 | 0.61 | 32.30 | 46.76 | 64.35 | 96.9 | 3.35 |
| Example 44 | 200 | 0 | 196 | 1.15 | 32.77 | 46.54 | 63.40 | 96.8 | 3.83 |
| Example 45 | 200 | −10 | 196 | 1.02 | 31.52 | 46.47 | 64.32 | 97.5 | 4.16 |
| Example 46 | 200 | −20 | 196 | 1.00 | 34.48 | 47.70 | 62.96 | 97.4 | 2.56 |
| Example 47 | 200 | 50 | 196 | 0.67 | 36.26 | 44.98 | 59.59 | 96.9 | 4.15 |
| Example 48 | 200 | 30 | 500 | 1.38 | 32.08 | 52.76 | 66.31 | 98.5 | 1.61 |
| Comparative Example 4 | 0 | 30 | 196 | 0.32 | 27.81 | 45.83 | 66.69 | 98 | 5.5 |

The data in Table 4 indicate that a high ethylene oligomerization activity is obtained in the presence of the catalyst composition according to the present disclosure which contains water. More specifically, from comparisons between the catalyst activity in Examples 37 to 43 to that in Comparative Example 4, it is obvious that, under the same oligomerization conditions, the activity of the catalyst composition according to the present disclosure is 1.8 to 4 times of that of the catalyst used in Comparative Example 4. Furthermore, the examples according to the present disclosure obtain as high a selectivity of α-olefins as Comparative Example 4 does. Particularly, when the content of water ranges from 50 ppm to 200 ppm, the ethylene oligomerization activity exceeds $1\times10^7$ g·mol $(Fe)^{-1}\cdot h^{-1}$. It is thus clear that the catalyst having a content of water within the above range is especially suitable for catalyzing ethylene oligomerization in industrial production. In addition, the oligomerization reaction according to the present disclosure is of rapid initiation, stable operation, and good repeatability.

Moreover, Table 4 shows that even when the ratio of Al to Fe is as low as 196, the catalyst of the present disclosure still has good activity for catalyzing the oligomerization reaction, thereby significantly reducing costs of ethylene oligomerization. Hence, the catalyst according to the present disclosure is of high practicability and has broad prospects for industrialization. Besides, the examples prove that according to the present disclosure, high oligomerization activity can still be obtained even at a low reaction temperature.

Example 49

1. Synthesis of 2-isobutyryl-1,10-phenanthroline (2,6-diethylanil) $FeCl_2$ Ligand a) Synthesis of 2-isobutyryl-1,10-phenanthroline 5.1 g (28.3 mmol) of 1,10-phenanthroline is put into a 250 ml, three-necked flask, and is dissolved into 100 ml of toluene under protection of nitrogen and magnetic stirring. 13.7 ml of $(i\text{-}C_4H_9)_3Al$ (d=0.82 g/ml, 56.6 mmol) is dropwise added into the three-necked flask under stirring at −60° C. in about 15 min, and the resulting mixture is stirred at the same temperature for 18 h. Afterwards, the resulting mixture is heated to about 30° C. and stirred for another 10 h. Next, the reaction mixture is cooled down to about −30° C. followed by slow addition of 50 ml of distilled water. Then the mixture is heated again to 30° C. and stirred for 10 h. Subsequently, liquid separation is performed and an organic phase is taken out. An inorganic phase is extracted with dichloromethane for three times, each time with an amount of 20 ml of dichloromethane.

The organic phases are combined. The solvent is removed under reduced pressure. Afterwards, 50 ml (1.205 g/ml) of nitrobenzene is added and refluxed for about 18 h at 210° C. After filtration, the nitrobenzene is removed under distillation at a pressure lower than 10 mmHg to obtain a black viscous liquid substance. A mixture solution of ethyl acetate and petroleum ether with a volume ratio of 1:2 is used as an eluent to perform silica column chromatography to the obtained black viscous liquid substance, so as to obtain a brown product, which weighs 2.1 g with a yield of 30%. The product, after nuclear magnetic resonance analysis and mass spectrometry, is determined as the compound as referred to under a), i.e., 2-isobutyryl-1,10-phenanthroline.

Mass spectrometry MS-EI: 250.

Nuclear magnetic resonance analysis: $^1H$ NMR (400 MHz, $CDCl_3$): δ9.26 (dd, J=1.72, 1 H); 8.33 (s, 2 H); 8.27 (dd, J=1.68, 1 H) 7.86 (d, J=8.8, 1 H); 7.80 (d, J=8.8, 1 H); 7.68 (dd, J=5.28, 1 H); 3.47 (m, J=7.24, 1 H); 1.10 (d, J=7.4, 6 H).

b) Synthesis of 2-isobutyryl-1,10-phenanthroline (2,6-diethylanil) Ligand 0.53 g (2.12 mmol) of 2-isobutyryl-1,10-phenanthroline obtained in step a), 0.95 g (6.36 mmol) of 2,6-diethylaniline with a molar ratio of 1:3, and 35 ml of toluene containing no water or oxygen are put into a 100 ml, two-necked flask having a manifold. The manifold is provided with a condenser pipe. 0.01 g of p-toluene sulfonic acid is added and refluxed at 110° C. After 6 h of reaction, the solvent is removed under reduced pressure. A mixture solution of ethyl acetate and petroleum ether with a volume ratio of 1:4 is used as an eluent to perform silica column chromatography to obtain a bright yellow product, which weighs 0.65 g with a yield of 81%. The product, after nuclear magnetic resonance analysis, mass spectrometry, and elemental analysis, is determined as the compound as referred to under h), i.e., 2-isobutyryl-1,10-phenanthroline (2,6-diethylanil).

Mass spectrometry MS-EI: 381.

Nuclear magnetic resonance analysis: $^1H$ NMR (400 MHz, $CDCl_3$): δ9.25 (dd, J=2.96, 1 H); 8.66 (d, J=8.36, 1 H); 8.33 (d, J=8.36, 1 H); 8.28 (dd, J=7.84, 1 H); 7.85 (dd, J=9.02, 2 H); 7.65 (dd, J=4.36, 1 H); 7.15 (d, J=7.52, 2 H); 7.06 (t, J=7.04, 1 H); 3.01 (m, J=7.84, —$CNCH(CH_3)_2$, 1 H); 2.40 (m, J=7.52, $phCH_2CH_3$, 4 H); 1.58 (d, J=7.44, —CNCH $(CH_3)_2$, 6 H); 1.20 (t, J=7.30, $phCH_2CH_3$, 6 H).

Elemental analysis: $C_{26}H_{27}N_3$ (381.51). Theoretical value: C, 81.85; H, 7.13; N, 11.01. Measured value: C, 81.36; H, 7.23; N, 10.55.

c) Synthesis of 2-isobutyryl-1,10-phenanthroline (2,6-diethylanil) $FeCl_2$

Under protection of nitrogen, 0.16 g (1.25 mmol) of $FeCl_2$ is dissolved into 20 ml of tetrahydrofuran containing no water or oxygen in a two-necked flask. 0.52 g (1.36 mmol) of 2-isobutyryl-1,10-phenanthroline (2,6-diethylanil) obtained in step b) is separately dissolved into 20 ml of tetrahydrofuran containing no water or oxygen. The above two solutions are then combined under protection of nitrogen at room temperature. The reaction occurs immediately and the solution takes on the color of ash black. The resultant is stirred overnight under protection of nitrogen at room temperature. The reaction is monitored by TLC until the 2-isobutyryl-1,10-phenanthroline (2,6-diethylanil) ligand substantially disappears. After suction filtration and washing with anhydrous diethyl ether, vacuum drying is performed to obtain a silver gray solid. The obtained solid is determined as the compound as referred to under c), i.e., 2-isobutyryl-1,10-phenanthroline (2,6-diethylanil) $FeCl_2$, the elemental analysis of which is as follows.

Elemental analysis: $C_{26}H_{27}Cl_2FeN_3$ (508.26). Theoretical value: C, 61.44; H, 5.35; N, 8.27. Measured value: C, 61.79; H, 5.60; N, 8.13.

2. The ethylene oligomerization reaction specifically comprises the following steps. (1) A stainless steel reaction kettle is replaced through operations such as high temperature drying, vacuum replacement, etc., so as to ensure an anhydrous and oxygen-free reaction system. (2) The reaction kettle is replaced with ethylene, so as to ensure an ethylene atmosphere in the reaction system. (3) The reaction kettle is added with water and toluene under adequate stirring. (4) 1.37 ml of a toluene solution of $Et_3Al$ (with a concentration of 715 mol/ml) is added into the reaction kettle. (5) 2 ml of a toluene solution of 2-isobutyryl-1,10-phenanthroline (anil) $FeCl_2$ (with a concentration of 2.5 μmol/ml) is added into the reaction kettle, ensuring a Al/Fe ratio of 196 and a water content of 5 ppm based on weight of toluene. Then ethylene is fed into the reaction kettle to perform the oligomerization reaction. (6) The oligomerization reaction is kept for 30 min under an ethylene pressure of 1 MPa at 30° C. (7) The reaction is stopped, and a small amount of reaction product is taken out for gas chromatography (GC) analysis. The oligomerization activity is $0.52 \times 10^7$ $g \cdot mol(Fe)^{-1} \cdot h^{-1}$. The oligomers contain 20.6% of $C_4$, 48.49% of $C_6$ to $C_{10}$, 72.24% (wherein α-olefins account for 98.2%) of $C_6$ to $C_{18}$, and 7.15% of $C_{20}$ to $C_{28}$. The value of K is 0.63. The remaining mixture is neutralized by an ethanol solution acidified with dilute hydrochloric acid of 5%, and no polymers are obtained. The analysis results are shown in Table 5.

Examples 50 to 56

The steps in Example 49 are repeated only with different contents of water and reaction parameters. The data are shown in Table 5.

Comparative Example 5

The steps of Example 49 are repeated only with 0 ppm of water. The data are shown in Table 5.

TABLE 5

| Number | Content of water (ppm) | T (° C.) | Al/Fe (mol) | Activity ($10^7$ g·mol$^{-1}$·h$^{-1}$) | $C_4$ (%) | $C_6$~$C_{10}$ (%) | $C_6$~$C_{18}$ Content (%) | $C_6$~$C_{18}$ Linear α-olefins (%) | $C_{20}$~$C_{28}$ (%) |
|---|---|---|---|---|---|---|---|---|---|
| Example 49 | 5 | 30 | 196 | 0.52 | 20.6 | 48.49 | 72.24 | 98.2 | 7.15 |
| Example 50 | 20 | 30 | 196 | 0.63 | 22.37 | 50.24 | 74.88 | 98 | 6.03 |
| Example 51 | 50 | 30 | 196 | 0.99 | 22.09 | 45.77 | 65.96 | 97.8 | 11.95 |
| Example 52 | 120 | 30 | 196 | 0.92 | 21.44 | 52.41 | 74.05 | 98 | 4.51 |
| Example 53 | 200 | 30 | 196 | 1.01 | 21.48 | 46.71 | 70.66 | 97.2 | 7.85 |
| Example 54 | 260 | 30 | 196 | 0.61 | 21.1 | 49.76 | 72.32 | 97 | 6.58 |
| Example 55 | 350 | 30 | 196 | 0.46 | 19.86 | 47.55 | 71.73 | 97 | 8.42 |
| Example 56 | 200 | 0 | 196 | 0.9 | 20.23 | 49.23 | 72.75 | 97.7 | 7.02 |
| Example 57 | 200 | −10 | 196 | 0.77 | 22.33 | 51.4 | 72.98 | 96 | 4.69 |
| Example 58 | 200 | −20 | 196 | 0.75 | 22.35 | 49.72 | 70.87 | 97.4 | 6.78 |
| Example 59 | 200 | 50 | 196 | 0.62 | 21.76 | 50.09 | 72.49 | 98.1 | 5.75 |
| Example 60 | 200 | 30 | 500 | 1.13 | 23.02 | 49.68 | 71.24 | 98.7 | 5.74 |
| Comparative Example 5 | 0 | 30 | 196 | 0.38 | 25.4 | 52.9 | 71.3 | 91.3 | 3.3 |

The data in Table 5 indicate that a high ethylene oligomerization activity is obtained in the presence of the catalyst composition according to the present disclosure which comprises the main catalyst, i.e., the 2-isobutyryl-acyl-1,10-phenanthroline (anil) $FeCl_2$ complex, the aluminum-containing cocatalyst (such as $Et_3Al$), water, and the organic solvent. Moreover, high selectivity of α-olefins can be obtained. Besides, even when the ratio of Al to Fe is rather low or when the reaction temperature is low, the oligomerization activity is still high. Particularly, when the content of water ranges from 50 ppm to 200 ppm, the ethylene oligomerization activity approaches $1 \times 10^7$ $g \cdot mol(Fe)^{-1} \cdot h^{-1}$. It is thus clear that the catalyst having a content of water within the above range is especially suitable for catalyzing ethylene oligomerization in industrial production.

Example 61

2-benzoyl-1,10-phenanthroline (2,6-diethylanil) $FeCl_2$ is used as the main catalyst.

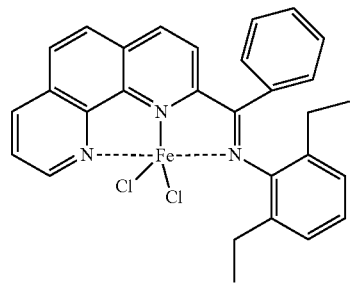

It comprises the following specific steps in using the catalyst composition for ethylene oligomerization. (1) The reaction system is replaced through operations such as high temperature drying, vacuum replacement, etc., so as to ensure an anhydrous and oxygen-free reaction system. (2) The reaction system is replaced with ethylene, so as to ensure an ethylene atmosphere in the reaction system. (3) A reaction kettle is added with a certain amount of hydrous toluene, 1.37 ml of a toluene solution of $Et_3Al$ (with a concentration of 715 μmol/ml), and 2 ml of a toluene solution of 2-benzoyl-1,10-phenanthroline (2,6-diethylanil) $FeCl_2$ (with a concentration of 2.5 μmol/ml). As a result, the total amount of the composition is 100 ml. The content of water based on weight of the organic solvent is 5 ppm, and the ratio of Al/Fe is 196. After adequate stirring, ethylene is fed into the kettle to perform the oligomerization reaction. (4) The oligomerization reaction is kept for 30 min under an ethylene pressure of 1 MPa at 30° C. (5) The reaction is stopped, and a small amount of reaction product is taken out for gas chromatography (GC) analysis.

In this example, the activity of the catalyst for catalyzing the ethylene oligomerization is $0.52 \times 10^7$ g·mol$(Fe)^{-1}$·h$^{-1}$. The oligomers contain 21.44% of $C_4$, 52.41% of $C_6$ to $C_{10}$, 74.05% (wherein α-olefins account for 98%) of $C_6$ to $C_{18}$, and 4.51% of $C_{20}$ to $C_{28}$. The remaining mixture is neutralized by an ethanol solution acidified with dilute hydrochloric acid of 5%, and no polymers are obtained. The analysis results are shown in Table 6.

Examples 62 to 72

The steps in Example 61 are repeated only with different contents of water and reaction parameters. The data are shown in Table 6.

Comparative Example 6

The steps of Example 61 are repeated only with 0 ppm of water. The data are shown in Table 6.

when the content of water ranges from 50 ppm to 200 ppm, the ethylene oligomerization activity exceeds $1 \times 10^7$ g·mol $(Fe)^{-1}$·h$^{-1}$. It is thus clear that a catalyst having a content of water within the above range is especially suitable for catalyzing ethylene oligomerization in industrial production. In addition, the oligomerization reaction according to the present disclosure is of rapid initiation, stable operation, and good repeatability.

Moreover, Table 6 shows that even when the ratio of Al to Fe is as low as 196, the catalyst of the present disclosure still has good activity for catalyzing the oligomerization reaction, thereby significantly reducing costs of ethylene oligomerization. Hence, the catalyst according to the present disclosure is of high practicability and has broad prospects for industrialization. Besides, the examples prove that, according to the present disclosure, high oligomerization activity can still be obtained even at a low reaction temperature.

Example 73

A 2,6-diacetyl pyridine (o-toluid) $FeCl_2$ complex is used as the main catalyst.

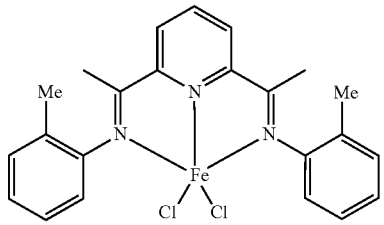

It comprises the following specific steps in using the catalyst composition for ethylene oligomerization. (1) The reac-

TABLE 6

|  | Content of water (ppm) | T (° C.) | Al/Fe (mol) | Activity ($10^7$ g·mol $(Fe)^{-1}$·h$^{-1}$) | $C_4$ (%) | $C_6$~$C_{10}$ (%) | $C_6$~$C_{18}$ | | $C_{20}$~$C_{28}$ (%) |
|---|---|---|---|---|---|---|---|---|---|
|  |  |  |  |  |  |  | Content (%) | Linear α-olefins (%) |  |
| Example 61 | 5 | 30 | 196 | 0.52 | 21.44 | 52.41 | 74.05 | 98 | 4.51 |
| Example 62 | 20 | 30 | 196 | 0.73 | 22.03 | 52.26 | 72.71 | 98 | 5.27 |
| Example 63 | 50 | 30 | 196 | 1.19 | 24.18 | 45.52 | 66.32 | 97.7 | 9.5 |
| Example 64 | 120 | 30 | 196 | 1.12 | 22.42 | 49.21 | 71.33 | 98 | 6.25 |
| Example 65 | 200 | 30 | 196 | 1.21 | 27.03 | 53.67 | 71.97 | 98.2 | 1 |
| Example 66 | 260 | 30 | 196 | 0.81 | 19.5 | 44.13 | 69.52 | 98.3 | 10.98 |
| Example 67 | 350 | 30 | 196 | 0.56 | 20.43 | 45.12 | 69.81 | 98.1 | 9.76 |
| Example 68 | 200 | 0 | 196 | 1.1 | 20.4 | 45.29 | 69.75 | 98.2 | 9.85 |
| Example 69 | 200 | −10 | 196 | 0.97 | 18.85 | 42.55 | 69.35 | 98 | 11.79 |
| Example 70 | 200 | −20 | 196 | 0.95 | 18.36 | 49.74 | 75.62 | 98.2 | 6.02 |
| Example 71 | 200 | 50 | 196 | 0.62 | 23.24 | 49.69 | 72.65 | 97.8 | 4.11 |
| Example 72 | 200 | 30 | 500 | 1.33 | 20.6 | 48.4 | 75.03 | 98.3 | 4.37 |
| Comparative Example 6 | 0 | 30 | 196 | 0.27 | 19.44 | 50.55 | 75.34 | 97.9 | 5.23 |

The data in Table 6 indicate that a high ethylene oligomerization activity is obtained in the presence of the catalyst composition according to the present disclosure which contains water. More specifically, from comparisons between catalyst activity in Examples 61 to 67 to that in Comparative Example 6, it is obvious that, under the same oligomerization conditions, the activity of the catalyst composition according to the present disclosure is 2 to 4.5 times of that of the catalyst used in Comparative Example 6. Furthermore, the examples according to the present disclosure obtain as high a selectivity of α-olefins as Comparative Example 6 does, Particularly, tion system is replaced through operations such as high temperature drying, vacuum replacement, etc., so as to ensure an anhydrous and oxygen-free reaction system. (2) The reaction system is replaced with ethylene, so as to ensure an ethylene atmosphere in the reaction system. (3) A reaction kettle is added with a certain amount of hydrous toluene, 1.37 ml of a toluene solution of $Et_3Al$ (with a concentration of 715 μmol/ml), and 2 ml of a toluene solution of the 2,6-diacetyl pyridine (o-toluid) $FeCl_2$ complex (with a concentration of 2.5 μmol/ml). As a result, the total amount of the composition is 100 ml. The content of water based on weight of the organic solvent is 5 ppm, and the ratio of Al/Fe is 196. After adequate stirring, ethylene is fed into the kettle to perform the oligomerization reaction. (4) The oligomerization reaction is kept for 30 min under an ethylene pressure of 1 MPa at 30° C. (5) The reaction is stopped, and a small amount of reaction product is taken out for gas chromatography (GC) analysis. The remaining mixture is neutralized by an ethanol solution acidified with dilute hydrochloric acid of 5%, and no polymers are obtained. The data are shown in Table 7.

Examples 74 to 84

The steps in Example 73 are repeated only with different contents of water and reaction parameters. The data are shown in Table 7.

Comparative Example 7

The steps of Example 73 are repeated only with 0 ppm of water. The data are shown in Table 7.

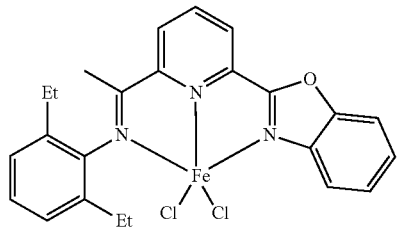

It comprises the following specific steps in using the catalyst composition for ethylene oligomerization. (1) The reaction system is replaced through operations such as high temperature drying, vacuum replacement, etc., so as to ensure an anhydrous and oxygen-free reaction system. (2) The reaction system is replaced with ethylene, so as to ensure an ethylene atmosphere in the reaction system. (3) A reaction kettle is added with a certain amount of hydrous toluene, 1.37 ml of a toluene solution of $Et_3Al$ (with a concentration of 715 μmol/ml), and 2 ml of a toluene solution of the 2-benzoxazolyl-6-acetyl (2,6-diethylanil) $FeCl_2$ complex (with a concentration of 2.5 μmol/ml). As a result, the total amount of the compo-

TABLE 7

| Number | Content of water (ppm) | T (° C.) | Al/Fe (mol) | Activity ($10^7$ g·mol(Fe)$^{-1}$·h$^{-1}$) | $C_4$ (%) | $C_6$~$C_{10}$ (%) | $C_6$~$C_{18}$ Content (%) | Linear α-olefins (%) | $C_{20}$~$C_{28}$ (%) |
|---|---|---|---|---|---|---|---|---|---|
| Example 73 | 5 | 50 | 196 | 0.56 | 29.13 | 57.12 | 9.65 | 94.5 | 1.22 |
| Example 74 | 20 | 50 | 196 | 0.72 | 26.35 | 55.53 | 71.03 | 95.4 | 2.62 |
| Example 75 | 50 | 50 | 196 | 1.42 | 17.32 | 52.33 | 75.24 | 96.8 | 7.44 |
| Example 76 | 120 | 50 | 196 | 1.56 | 18.13 | 55.23 | 76.24 | 97.2 | 5.63 |
| Example 77 | 200 | 50 | 196 | 1.22 | 19.01 | 51.32 | 74.21 | 96.2 | 6.78 |
| Example 78 | 260 | 50 | 196 | 0.54 | 21.43 | 52.03 | 71.81 | 95.4 | 6.76 |
| Example 79 | 350 | 50 | 196 | 0.24 | 26.52 | 58.22 | 70.06 | 94.7 | 3.42 |
| Example 80 | 120 | 40 | 196 | 1.14 | 19.18 | 52.33 | 74.85 | 96.9 | 5.97 |
| Example 81 | 120 | 20 | 196 | 0.83 | 22.65 | 48.23 | 72.57 | 96.6 | 4.78 |
| Example 82 | 120 | 10 | 196 | 0.71 | 24.53 | 45.14 | 70.25 | 95.1 | 5.22 |
| Example 83 | 120 | 70 | 196 | 0.92 | 23.15 | 49.12 | 70.59 | 96.4 | 6.26 |
| Example 84 | 120 | 50 | 500 | 1.33 | 22.87 | 51.72 | 70.90 | 97.1 | 6.23 |
| Comparative Example 7 | 0 | 50 | 196 | 0.12 | 26.20 | 51.52 | 70.02 | 94.1 | 3.78 |

The data in Table 7 indicate that a high ethylene oligomerization activity is obtained in the presence of the catalyst composition according to the present disclosure which comprises the main catalyst, i.e., the 2,6-diacetyl pyridine (o-toluid) $FeCl_2$ complex, the aluminum-containing cocatalyst (such as $Et_3Al$), water, and the organic solvent. Moreover, high selectivity of α-olefins can be obtained. The catalytic activity of the oligomerization reaction system reaches as high as $1.56×10^7$ g·mol(Fe)$^{-1}$·h$^{-1}$, which is 10 times higher than the catalytic activity under the same conditions only with the catalyst containing no water. Besides, even when the ratio of Al to Fe is rather low, the oligomerization activity is still high. Particularly, when the content of water ranges from 50 ppm to 200 ppm, the ethylene oligomerization activity exceeds $1×10^7$ g·mol(Fe)$^{-1}$·h$^{-1}$. It is thus clear that the catalyst having a content of water within the above range is especially suitable for catalyzing ethylene oligomerization in industrial production.

Example 85

A 2-benzoxazolyl-6-acetyl (2,6-diethylanil) $FeCl_2$ complex is used as the main catalyst.

sition is 100 ml. The content of water based on weight of the organic solvent is 5 ppm, and the ratio of Al/Fe is 196. After adequate stirring, ethylene is fed into the kettle to perform the oligomerization reaction. (4) The oligomerization reaction is kept for 30 min under an ethylene pressure of 1 MPa at 30° C. (5) The reaction is stopped, and a small amount of reaction product is taken out for gas chromatography (GC) analysis. The remaining reaction mixture is neutralized by an ethanol solution acidified with dilute hydrochloric acid of 5%, and no polymers are obtained. The data are shown in Table 8.

Examples 86 to 96

The steps in Example 85 are repeated only with different contents of water and reaction parameters. The data are shown in Table 8.

Comparative Example 8

The steps of Example 85 are repeated only with 0 ppm of water. The data are shown in Table 8.

TABLE 8

Experiment results of ethylene oligomerization

| | Content of water (ppm) | T (° C.) | Al/Fe (mol) | Activity ($10^7$ g·mol$(Fe)^{-1}$·h$^{-1}$) | $C_4$ (%) | $C_6$~$C_{10}$ (%) | $C_6$~$C_{18}$ Content (%) | Linear α-olefins (%) | $C_{20}$~$C_{28}$ (%) |
|---|---|---|---|---|---|---|---|---|---|
| Example 85 | 5 | 30 | 196 | 0.43 | 41.22 | 47.34 | 58.20 | 96.4 | 0.58 |
| Example 86 | 20 | 30 | 196 | 0.66 | 45.32 | 36.78 | 53.98 | 96.1 | 0.70 |
| Example 87 | 50 | 30 | 196 | 0.91 | 44.52 | 37.05 | 54.66 | 97.3 | 0.82 |
| Example 88 | 100 | 30 | 196 | 1.08 | 31.50 | 47.28 | 65.84 | 96.3 | 2.66 |
| Example 89 | 200 | 30 | 196 | 0.95 | 31.68 | 44.21 | 62.99 | 95.4 | 5.33 |
| Example 90 | 260 | 30 | 196 | 0.63 | 35.44 | 44.62 | 60.70 | 96.1 | 3.86 |
| Example 91 | 350 | 30 | 196 | 0.42 | 34.56 | 47.21 | 63.30 | 96.1 | 2.14 |
| Example 92 | 100 | 0 | 196 | 0.97 | 33.90 | 45.62 | 62.75 | 95.2 | 3.35 |
| Example 93 | 100 | −10 | 196 | 0.86 | 32.65 | 46.58 | 63.33 | 96.2 | 4.02 |
| Example 94 | 100 | −20 | 196 | 0.71 | 35.80 | 48.22 | 61.68 | 96.1 | 2.52 |
| Example 95 | 100 | 40 | 196 | 0.52 | 36.16 | 44.81 | 61.81 | 95.8 | 2.03 |
| Example 96 | 100 | 30 | 500 | 1.01 | 34.64 | 52.22 | 64.29 | 97.6 | 1.07 |
| Comparative Example 8 | 0 | 30 | 196 | 0.09 | 30.82 | 46.80 | 65.62 | 97.3 | 3.56 |

The data in Table 8 indicate that a high ethylene oligomerization activity is obtained in the presence of the catalyst composition according to the present disclosure which comprises the main catalyst, i.e., the 2-benzoxazolyl-6-acetyl (2,6-diethylanil) FeCl$_2$ complex, the aluminum-containing cocatalyst (such as Et$_3$Al), water, and the organic solvent. Moreover, high selectivity of α-olefins can be obtained. The catalytic activity of the oligomerization reaction system reaches as high as $1.08 \times 10^7$ g·mol(Fe)$^{-1}$·h$^{-1}$, which is 10 times higher than the catalytic activity under the same conditions only with the catalyst containing no water. Besides, even when the ratio of Al to Fe is rather low, the oligomerization activity is still high. Particularly, when the content of water ranges from 50 ppm to 200 ppm, the ethylene oligomerization activity exceeds $1 \times 10^7$ g·mol(Fe)$^{-1}$·h$^{-1}$. It is thus clear that the catalyst having a content of water within the above range is especially suitable for catalyzing ethylene oligomerization in industrial production.

The above data prove that when used in ethylene oligomerization, the catalyst composition according to the present disclosure can promote a high oligomerization activity, with high selectivity of α-olefins. Even the oligomerization is carried out with rather a low ratio of Al/Fe or at a low reaction temperature, high oligomerization activity can still be obtained.

It should be noted that the above examples are only used to explain, rather than to limit the present disclosure in any manner. Although the present disclosure has been discussed with reference to preferable examples, it should be understood that the terms and expressions adopted are for describing and explaining instead of limiting the present disclosure. The present disclosure can be modified within the scope of the claims, or can be amended without departing from the range or spirits of the present disclosure. Although the present disclosure is described with specific methods, materials, and examples, the scope of the present disclosure herein disclosed should not be limited by the particular disclosed examples as described above, but can be extended to other methods and uses having the same functions.

The invention claimed is:

1. A catalyst composition for ethylene oligomerization, comprising an imino ferrous complex shown in Formula (II) as a main catalyst, an aluminum-containing cocatalyst, water, and an organic solvent,

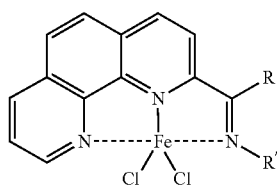

(II)

wherein R is selected from the group consisting of hydrogen, oxygen, and ($C_1$-$C_{10}$) linear alkyl, ($C_3$-$C_{10}$) branched alkyl, ($C_6$-$C_{20}$) aryl, ($C_7$-$C_{20}$) aralkyl, and ($C_7$-$C_{20}$) alkaryl groups; and R' is selected from the group consisting of substituted or unsubstituted ($C_6$-$C_{20}$) aryl, ($C_7$-$C_{20}$) aralkyl, and ($C_7$-$C_{20}$) alkaryl groups, wherein based on weight of the organic solvent, the catalyst composition has a content of water in a range from 5 to 450 ppm.

2. The catalyst composition according to claim 1, wherein the main catalyst imino ferrous complex has a general formula as shown in Formula (II):

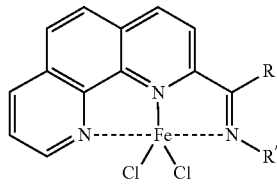

(II)

wherein R is selected from the group consisting of hydrogen, and ($C_1$-$C_5$) linear alkyl, ($C_3$-$C_6$) branched alkyl, ($C_6$-$C_{10}$) aryl, ($C_7$-$C_{10}$) aralkyl, and ($C_7$-$C_{10}$) alkaryl groups; or R' is selected from the group consisting of substituted or unsubstituted phenyl, naphthyl, ($C_7$-$C_{20}$) aralkyl, and ($C_7$-$C_{20}$) alkaryl groups.

3. The catalyst composition according to claim 1, wherein the main catalyst imino ferrous complex has a general formula as shown in Formula (III):

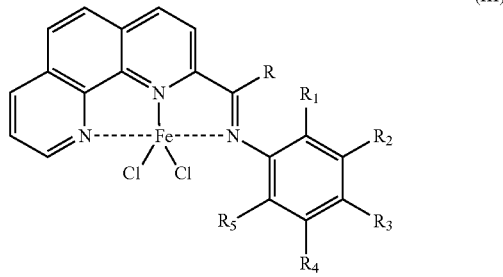

wherein $R_1$ to $R_5$ each are independently selected from the group consisting of hydrogen, ($C_1$-$C_6$) alkyl groups, halogens, ($C_1$-$C_6$) alkoxy or nitro groups; and R is selected from the group consisting of hydrogen, ($C_1$-$C_5$) linear alkyl, ($C_3$-$C_6$) branched alkyl, ($C_6$-$C_{10}$) aryl, ($C_7$-$C_{10}$) aralkyl, and ($C_7$-$C_{10}$) alkaryl groups.

4. The catalyst composition according to claim 3, wherein in Formula (III), R is selected from the group consisting of hydrogen, and methyl, ethyl, propyl, isopropyl, butyl, isobutyl, tert-butyl, pentyl, phenyl, benzyl, tolyl, and phenethyl groups; and $R_1$ to $R_5$ each are independently selected from the group consisting of hydrogen, methyl, ethyl, n-propyl, and isopropyl groups, fluorine, chlorine, bromine, and methoxy, ethoxy and nitro groups.

5. The catalyst composition according to claim 4, wherein $R_1$ and $R_5$ both are ethyl groups, and $R_2$ to $R_4$ are all hydrogen.

6. The catalyst composition according to claim 1, wherein based on weight of the organic solvent, the catalyst composition has a content of water in a range from 5 to 350 ppm.

7. The catalyst composition according to claim 1, wherein based on weight of the organic solvent, the catalyst composition has a content of water in a range from 20 to 260 ppm.

8. The catalyst composition according to claim 1, wherein based on weight of the organic solvent, the catalyst composition has a content of water in a range from 50 to 200 ppm.

9. The catalyst composition according to claim 1, wherein a molar ratio of aluminum in the cocatalyst to iron in the main catalyst ranges from 30:1 to less than 900:1.

10. The catalyst composition according to claim 1, wherein a molar ratio of aluminum in the cocatalyst to iron in the main catalyst ranges from 100:1 to 700:1.

11. The catalyst composition according to claim 1, wherein a molar ratio of aluminum in the cocatalyst to iron in the main catalyst ranges from 148:1 to 196:1.

12. The catalyst composition according to claim 1, wherein the aluminum-containing cocatalyst is selected from the group consisting of aluminoxanes and alkylaluminum compounds.

13. The catalyst composition according to claim 12, wherein the alkylaluminum compounds have a general formula of $AlR_nX_m$, wherein R is a linear or branched ($C_1$-$C_8$) alkyl group; and X is a halogen, with n being an integral ranging from 1 to 3, m an integral ranging from 0 to 2, and m+n=3.

14. The catalyst composition according to claim 13, wherein the halogen is chlorine or bromine; or the alkylaluminum compounds are selected from the group consisting of trimethylaluminum, triethylaluminum, tripropylaluminum, triisobutylaluminum, tri-n-hexyl aluminum, tri-n-octyl aluminum, diethyl aluminum chloride, and ethyl aluminum dichloride.

15. The catalyst composition according to claim 12, wherein the aluminoxanes are ($C_1$-$C_4$) alkylaluminoxanes with linear or branched ($C_1$-$C_4$) alkyl groups.

16. The catalyst composition according to claim 10, wherein the aluminoxanes are selected from the group consisting of methylaluminoxane, modified methylaluminoxane, ethylaluminoxane, and isobutyl aluminoxane.

17. The catalyst composition according to claim 1, wherein based on volume of the organic solvent, the catalyst composition has a content of the main catalyst in a range from 2 to 500 μmol/L.

18. The catalyst composition according to claim 1, wherein based on volume of the organic solvent, the catalyst composition has a content of the main catalyst in a range from 20 to 100 μmol/L.

19. The catalyst composition according to claim 1, wherein the organic solvent is selected from the group consisting of toluene, cyclohexane, diethyl ether, tetrahydrofuran, ethanol, benzene, xylene, and dichloromethane.

20. A process for ethylene oligomerization, comprising performing the ethylene oligomerization in the presence of the catalyst composition according to claim 1.

21. The process according to claim 20, wherein the process is performed at a temperature in the range from −20 °C. to 150 °C.

22. The process according to claim 20, wherein the process comprises mixing the main catalyst and the cocatalyst under ethylene atmosphere.

23. The process according to claim 20, wherein the process is performed at a temperature in the range from 0 °C to 80 °C.

24. The process according to claim 20, wherein the process is performed at a temperature in the range from 5 °C to 35 °C.

* * * * *